(12) United States Patent
Jones et al.

(10) Patent No.: US 9,962,269 B2
(45) Date of Patent: May 8, 2018

(54) IMPLANT WITH INDEPENDENT ENDPLATES

(71) Applicant: HD LifeSciences LLC, Stoneham, MA (US)

(72) Inventors: Christopher L. Jones, Winthrop, MA (US); Ian Helmar, Beverly, MA (US); Lucas Diehl, Beverly, MA (US); Jason Tinley, Fort Worth, TX (US); Kevin D. Chappuis, Malden, MA (US)

(73) Assignee: HD LifeSciences LLC, Stoneham, MA (US)

( * ) Notice: Subject to any disclaimer, the term of this patent is extended or adjusted under 35 U.S.C. 154(b) by 0 days. days.

(21) Appl. No.: 15/615,227

(22) Filed: Jun. 6, 2017

(65) Prior Publication Data

US 2017/0348114 A1 Dec. 7, 2017

Related U.S. Application Data

(60) Provisional application No. 62/346,720, filed on Jun. 7, 2016.

(51) Int. Cl.
*A61F 2/44* (2006.01)
*A61F 2/30* (2006.01)

(52) U.S. Cl.
CPC .......... *A61F 2/4455* (2013.01); *A61F 2/4425* (2013.01); *A61F 2/442* (2013.01);
(Continued)

(58) Field of Classification Search
CPC ............................................. A61F 2/44–2/447
(Continued)

(56) References Cited

U.S. PATENT DOCUMENTS 5,674,294 A 10/1997 Bainville et al.
2006/0259144 A1* 11/2006 Trieu .................... A61F 2/4425
623/17.13
(Continued)

FOREIGN PATENT DOCUMENTS

WO WO 2015164982 A1 * 11/2015 ............. A61L 27/56
WO 2016061148 A1 4/2016

OTHER PUBLICATIONS

International Search Report and Written Opinion received in Corresponding PCT Application, PCT/US2017/36111, dated Nov. 6, 2017; 14 pages.

*Primary Examiner* — Nicholas Plionis
(74) *Attorney, Agent, or Firm* — Law Office of Daniel A. Tesler, LLC; Reza Mollaaghababa; Ashley T. Brzezinski

(57) ABSTRACT

In some aspects, the present invention is a medical implant with an independent endplate structure that can stimulate bone or tissue growth in or around the implant. When used as a scaffold for bone growth, the inventive structure can increase the strength of new bone growth. The independent endplate structures generally include implants with endplates positioned on opposite sides of the implant and capable of movement independent of one another. In most examples, the endplates have a higher elastic modulus than that of the bulk of the implant to allow the use of an implant with a low elastic modulus, without risk of damage from the patient's bone.

A method of designing independent endplate implants is also disclosed, including ranges of elastic moduli for the endplates and bulk of the implant for given implant parameters. Implants with elastic moduli within the ranges disclosed herein can optimize the loading of new bone growth to provide increased bone strength.

20 Claims, 22 Drawing Sheets

(52) U.S. Cl.
CPC ..... *A61F 2/447* (2013.01); *A61F 2002/30006* (2013.01); *A61F 2002/30014* (2013.01); *A61F 2002/30546* (2013.01); *A61F 2002/443* (2013.01)

(58) Field of Classification Search
USPC .......................................... 623/17.11–17.16
See application file for complete search history.

(56) References Cited

U.S. PATENT DOCUMENTS

| | | | |
|---|---|---|---|
| 2008/0269903 A1* | 10/2008 | Francis | A61F 2/442 623/17.16 |
| 2009/0037148 A1 | 2/2009 | Lin et al. | |
| 2009/0317278 A1* | 12/2009 | Kokubo | A61L 27/06 419/2 |
| 2012/0022653 A1* | 1/2012 | Kirschman | A61F 2/447 623/17.16 |
| 2012/0150299 A1* | 6/2012 | Ergun | B29C 47/6037 623/17.11 |
| 2012/0179258 A1* | 7/2012 | Glazer | A61F 2/4425 623/17.16 |
| 2014/0277482 A1 | 9/2014 | Gfeller et al. | |
| 2015/0005885 A1 | 1/2015 | Zhang et al. | |
| 2016/0022431 A1* | 1/2016 | Wickham | A61F 2/447 623/17.16 |
| 2016/0038301 A1 | 2/2016 | Wickham | |

* cited by examiner

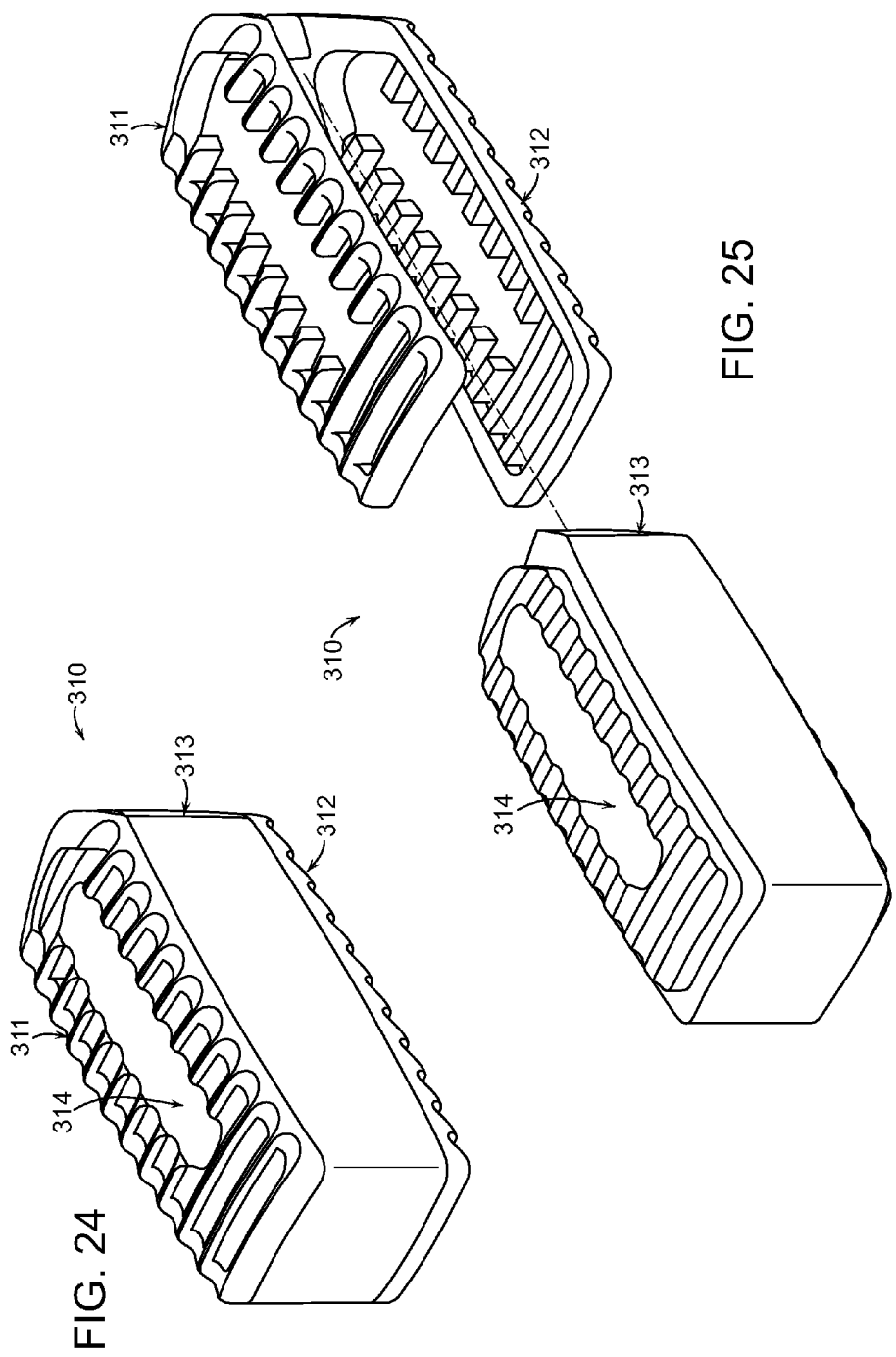

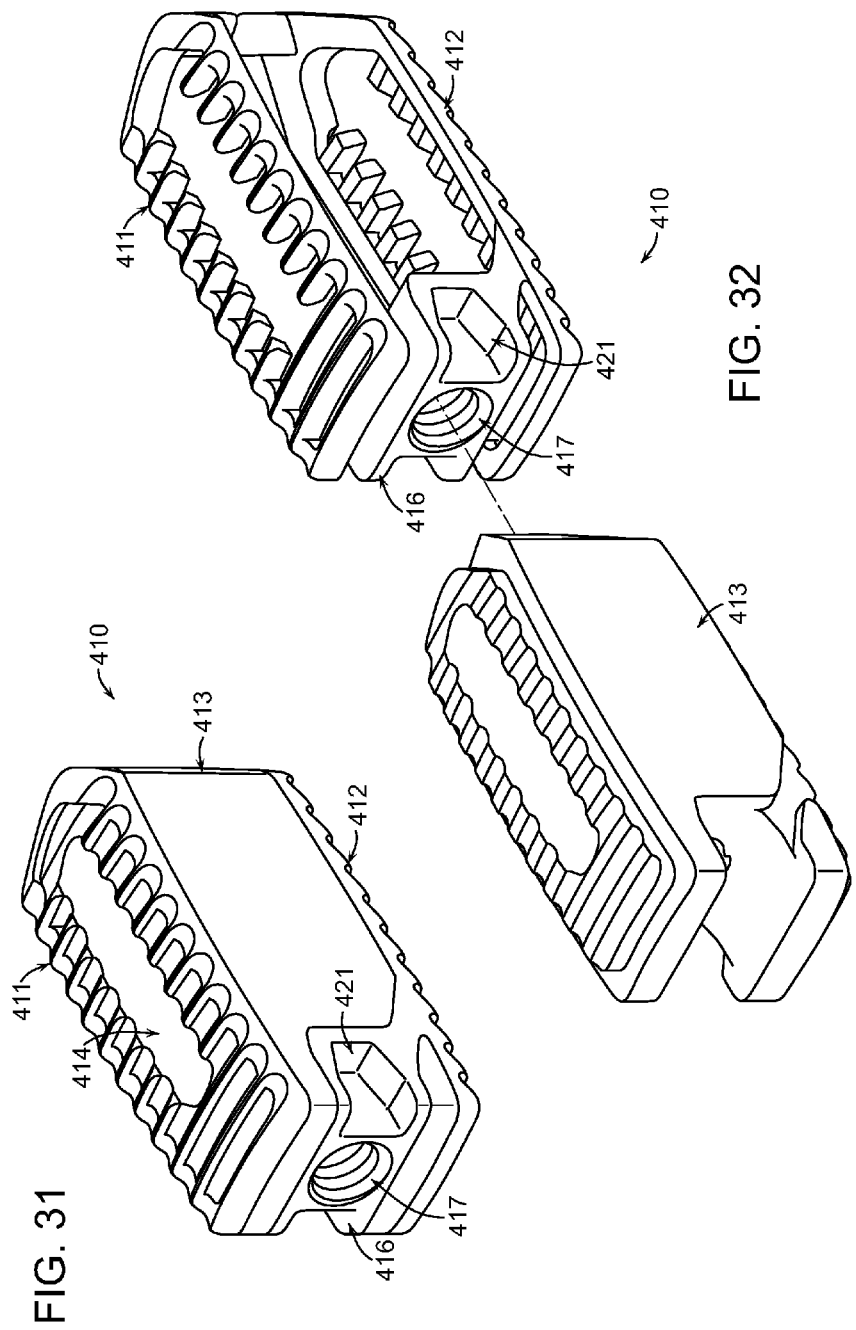

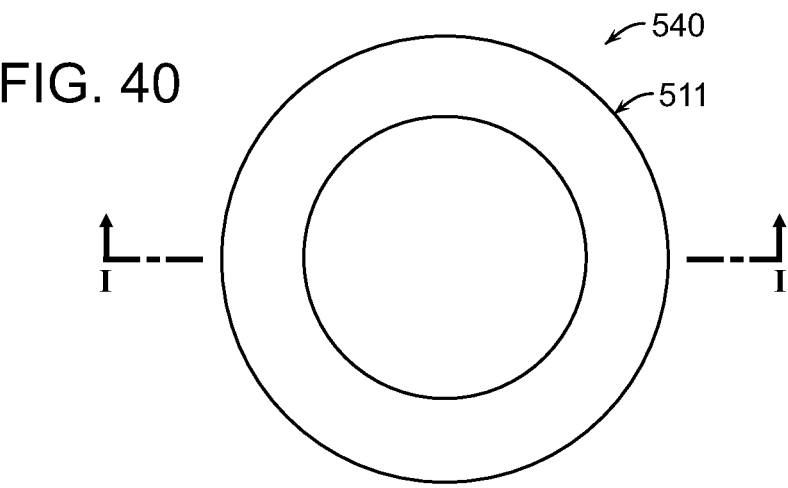
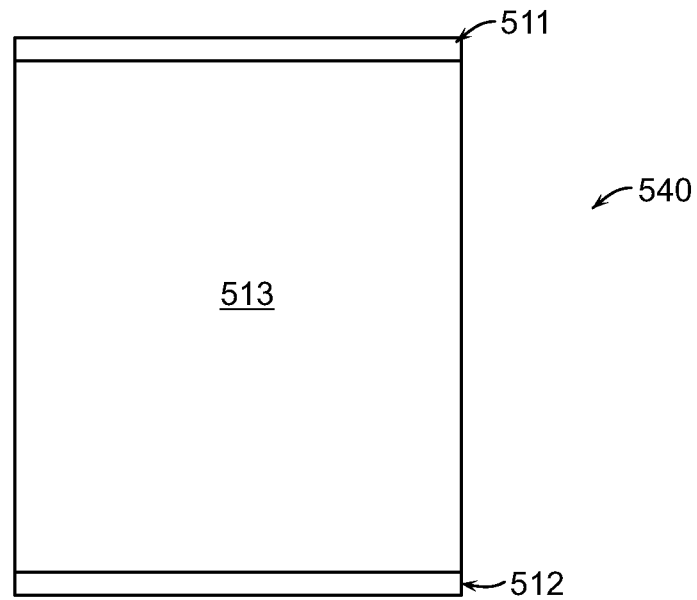

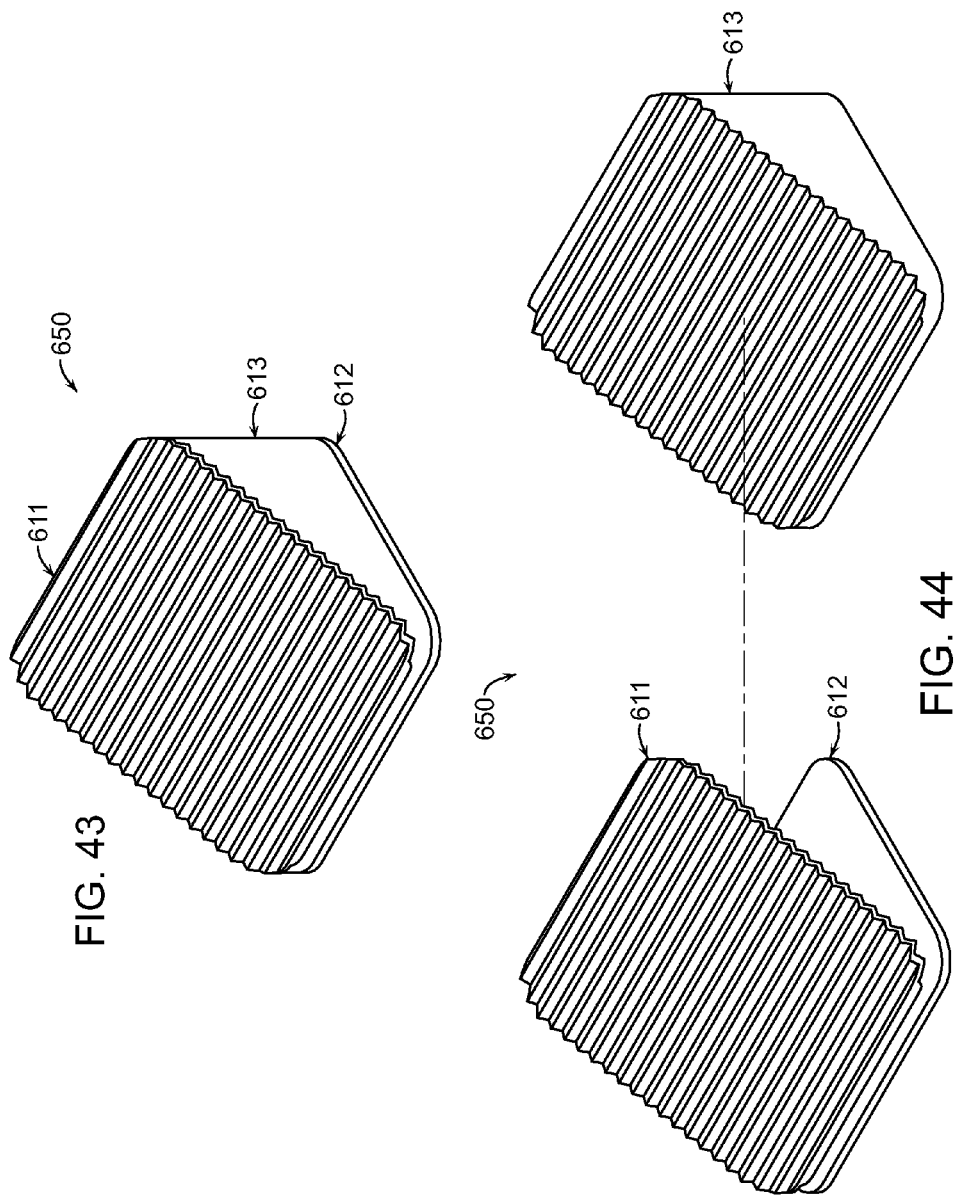

IMPLANT WITH INDEPENDENT ENDPLATES

CROSS REFERENCE TO RELATED APPLICATIONS

This application claims the benefit of U.S. Provisional Patent Application No. 62/346,720 filed Jun. 7, 2016, which is hereby incorporated by reference in its entirety.

FIELD OF THE INVENTION

The present invention relates to medical implants, in particular, to medical implants with independent endplates.

BACKGROUND OF THE INVENTION

Medical implants can be constructed using a wide range of materials, including metallic materials, Polyether ether ketone (hereinafter "PEEK"), ceramic materials and various other materials or composites thereof. There are competing priorities when selecting a material for an implant in order for the implant to pass regulatory testing. Some priorities when designing an implant could include strength, stiffness, fatigue resistance and radiolucency, and often some compromise is made during the design process.

For example, to meet the strength requirements for an implant, the radiolucency may be less than ideal for clinical assessment. As another example, to meet fatigue resistance standards, an implant may be designed with a higher than ideal stiffness for clinical applications.

BRIEF SUMMARY OF THE INVENTION

The present invention provides systems and methods of providing medical implants with two or more independent surfaces. Some embodiments disclosed herein can be used to provide structural support or mechanical spacing. In other embodiments, the structures disclosed herein can provide a scaffold for bone growth. In some aspects, the present invention provides an interbody fusion device that can be implanted between adjacent bones or bone fragments to provide mechanical spacing and a level of mechanical stabilization above the amount required for bone growth but without causing unnecessary stress shielding.

Implants which aid in bone growth can be used in many types of joints, including the bones of the hands and feet or even in the fracture of a single bone. Some examples shown in this application have been adapted for use between adjacent vertebrae. Although some examples presented in this application are optimized for use between adjacent vertebrae, it is appreciated that the invention could be used in other types of adjacent bones or bone fragments within the inventive concept expressed herein. The present invention can be useful in many types of implants, including but not limited to, cervical, lumbar, and thoracic interbody fusion implants, vertebral body replacements, osteotomy wedges, dental implants, bone stems, acetabular cups, cranio-facial plating, bone replacement and fracture plating. Interbody fusion-type devices include implants for the spine and can be designated based on their location (e.g. cervical, thoracic, lumbar) or their intended surgical procedure (e.g. anterior lumbar interbody fusion, posterior lumbar interbody fusion, transforaminal lumbar interbody fusion).

Interbody fusion devices are commonly used in surgical procedures to alleviate chronic joint pain and neurological symptoms by increasing vertebral spacing and allowing the two adjacent bones to fuse together. For instance, in cases where back pain is caused by diseased or degenerated disc material between adjacent vertebrae, spinal fusion surgery can provide a patient with relief from chronic pain. Spinal fusion surgery normally includes the removal of the damaged disc material between adjacent vertebrae and the insertion of an interbody fusion device to provide the mechanical spacing previously provided by the removed disc and to provide mechanical stabilization between the adjacent vertebrae to allow them to fuse together over time. According to Wolff's Law, bone will adapt to stresses placed on it so that bone under stress will grow stronger and bone that isn't stressed will become weaker. In some embodiments, the present invention provides an interbody fusion device with a construct elastic modulus similar to that of the surrounding bone when implanted. By providing independent endplates, the body of the device can be optimized to provide a specific elastic modulus without interference from a rigidly connected endplate structure. Even without a rigidly connected endplate structure, some embodiments expressed herein can provide adequate mechanical spacing between the endplates of adjacent vertebrae. By having an implant body with an optimized elastic modulus and independent endplates, in some aspects, the present invention can stimulate new bone growth and increase the strength of new bone growth through the implant.

In some embodiments, the present invention is comprised of a substantially rigid upper endplate and a substantially rigid lower endplate attached to opposite ends of a body. For clarity and ease of understanding, directions within the figures are described as front, back, right side, left side, top and bottom. The top and bottom of the implants can correspond to the superior and inferior directions, respectively, when implanted in a human spine. The term front refers to the leading edge of the implant when being inserted during implantation. The term back refers to the end opposite the front. The term right side refers to the right side of the implant when viewed from above and the term left side refers to the side opposite the right side. These specific directional references are exemplary and used to the example orientations described herein.

In some examples, the upper and lower endplates are comprised of a substantially rigid biocompatible material, such as titanium or any alloys thereof, and capable of distributing the load asserted by the endplates of the adjacent vertebrae across the body of the device. In some examples, the body is comprised of a material with a lower elastic modulus in the superior to inferior direction than the endplates to provide an adequate amount of stabilization for bone growth between the adjacent vertebrae, but also enough flexibility to prevent undue stress shielding. In some examples, the body is comprised of a material that provides a scaffold for new bone growth, such as a metallic lattice or scaffold structure.

The inventive independent endplate and lattice construction disclosed herein can increase the volume of space available for bone or tissue ingrowth, increase the surface area for bone or tissue attachment and increase radiolucency. Providing an implant with endplates having a higher elastic modulus than the body provides the implant with resistance from surface deformations that can compromise the structural properties of a lattice while allowing the use of a body with a lower modulus of elasticity, increasing the loading of new bone growth. The increased loading on the new bone growth tends to stimulate bone growth and results in higher strength bone growth. It has been found that specific ratios of elastic moduli between the endplates and the body optimize the benefits of reduced surface deformation and increased bone loading.

The independent endplate implant construction disclosed herein is shown in exemplary embodiments, including spinal interbody devices, a vertebral body replacement implant and an osteotomy wedge. While only a limited number of exemplary embodiments are shown, the independent endplate configuration can be used into other type of implants, especially other implants configured to attach to bone. Specifically, the independent endplate configuration would also be beneficial in dental applications to load new bone growth.

BRIEF DESCRIPTION OF THE SEVERAL VIEWS OF THE DRAWINGS

FIG. 24 is an isometric view of a second PLIF/TLIF implant showing the inventive configuration of the endplates relative to the body on the exterior of the device.

FIG. 25 is an exploded isometric view of a second PLIF/TLIF implant showing the endplates separated from the body.

FIG. 31 is an isometric view of a third PLIF/TLIF implant showing the inventive configuration of the endplates relative to the body on the exterior of the device.

FIG. 32 is an exploded isometric view of a third PLIF/TLIF implant showing the endplates separated from the body.

FIG. 40 is a top view of the VBR implant showing a possible configuration of an endplate top surface and the location of a later presented section view.

FIG. 41 is a rear view of the VBR implant configured without a rear tool engagement area.

FIG. 43 is an isometric view of an osteotomy wedge showing the inventive configuration of the endplates relative to the body on the exterior of the device.

FIG. 44 is an exploded isometric view of an osteotomy wedge showing the endplates separated from the body.

DETAILED DESCRIPTION OF THE INVENTION

Figure 1:
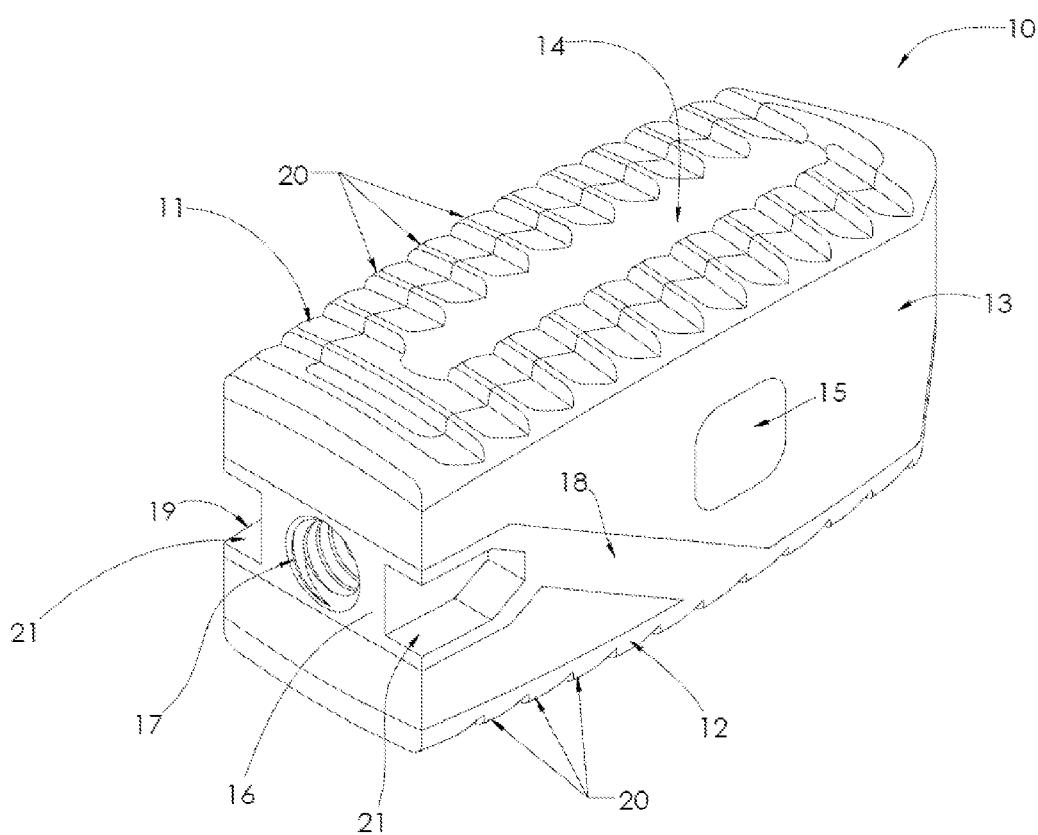
FIG. 1 is an isometric view of a posterior lumbar implant fusion (hereinafter "PLIF") or transforaminal lumbar implant fusion (hereinafter "TLIF") implant showing the inventive configuration of the endplates relative to the body on the exterior of the device.

In many situations, it is desirable to use an implant that is capable of bone attachment or osteointegration over time. Examples of implants where attachment to bone or osteointegration is beneficial include, but are not limited to, cervical, lumbar, and thoracic interbody fusion implants, vertebral body replacements, osteotomy wedges, dental implants, bone stems, acetabular cups, cranio-facial plating, bone replacement and fracture plating. In many applications, it is also desirable to stress new bone growth to increase its strength. According to Wolff's law, bone will adapt to stresses placed on it so that bone under stress will grow stronger and bone that isn't stressed will become weaker.

In some aspects, the systems and methods described herein can be directed toward implants that are configured for osteointegration and stimulating adequately stressed new bone growth. The exemplary implants of the present invention are particularly useful for use in situations where it is desirable to have strong bone attachment and/or bone growth throughout the body of an implant. Whether bone growth is desired only for attachment or throughout an implant, the present invention incorporates a unique lattice structure that can provide mechanical spacing, a scaffold to support new bone growth and a modulus of elasticity that allows new bone growth to be loaded with physiological forces. As a result, the present invention provides implants that grow stronger and healthier bone for more secure attachment and for a stronger bone after the implant osteointegrates.

The exemplary embodiments of the invention presented can be comprised, in whole or in part, of a lattice. A lattice, as used herein, refers to a three-dimensional material with one or more interconnected openings that allow a fluid to communicate from one opening to another location. A three-dimensional material refers to a material that fills a three-dimensional space (i.e. has height, width and length). Lattices can be constructed by many means, including repeating various geometric shapes or repeating random shapes to accomplish a material with interconnected openings. An opening in a lattice is any area within the bounds of the three-dimensional material that is devoid of that material. Therefore, within the three-dimensional boundaries of a lattice, there is a volume of material and a volume that is devoid of that material.

The material that provides the structure of the lattice is referred to as the primary material. The structure of a lattice does not need to provide structural support for any purpose, but rather refers to the configuration of the openings and interconnections that comprise the lattice. An opening in a lattice may be empty, filled with a gaseous fluid, filled with a liquid fluid, filled with a solid or partially filled with a fluid and/or solid. Interconnections, with respect to openings, refer to areas devoid of the primary material and that link at least two openings together. Interconnections may be configured to allow a fluid to pass from one opening to another.

A lattice can be defined by its volumetric density, meaning the ratio between the volume of the primary material and the volume of voids presented as a percentage for a given three-dimensional material. The volume of voids is the difference between the volume of the bounds of the three-dimensional material and the volume of the primary material. The volume of voids can be comprised of the volume of the openings, the volume of the interconnections and/or the volume of another material present. For example, a lattice with a 30% volumetric density would be comprised of 30% primary material by volume and 70% voids by volume over a certain volume. A lattice with a 90% volumetric density would be comprised of 90% primary material by volume and 10% voids by volume over a certain volume. In three-dimensional materials with a volumetric density of less than 50%, the volume of the primary material is less than the volume of voids. While the volumetric density refers to the volume of voids, the voids do not need to remain void and can be filled, in whole or in part, with a fluid or solid prior to, during or after implantation.

Lattices comprised of repeating geometric patterns can be described using the characteristics of a repeating unit cell. A unit cell in a repeating geometric lattice is a three-dimensional shape capable of being repeated to form a lattice. Each unit cell is comprised of a certain volume of primary material and a certain void volume, or in other words, a spot volumetric density. The spot volumetric density may cover as few as a partial unit cell or a plurality of unit cells. In most situations, the spot volumetric density will be consistent with the material's volumetric density, but there are situations where it could be desirable to locally increase or decrease the spot volumetric density. Unit cells can be constructed in numerous shapes or structures and are generally described based on the unit cell shape. Unit cells may be interconnected in some or all areas, not interconnected in some or all areas, of a uniform size in some or all areas or of a nonuniform size in some or all areas. In some embodiments disclosed herein that use a repeating geometric pattern, the unit cells can be defined by a number of struts defining the edges of the unit cell and joined at nodes about the unit cell. Unit cells so defined can share certain struts among more than one unit cell, so that two adjacent unit cells may share a common planar wall defined by struts common to both cells. In some embodiments disclosed herein that use a repeating geometric pattern, the unit cells can be defined by a node and a number of struts extending radially from that node. Such unit cells may be identical or substantially unique throughout a structure, and may be grouped into clusters, layers, or other configurations throughout a structure.

While the present application uses volumetric density to describe exemplary embodiments, it would also be possible to describe them using other metrics, including but not limited to cell size, strut size or stiffness. Cell size may be defined using multiple methods, including but not limited to cell diameter and cell volume. Strut size may be defined using multiple methods, including but not limited to strut length and strut diameter.

Repeating geometric patterns are beneficial for use in lattices contained in implants because they can provide predictable characteristics. Many repeating geometric shapes may be used as the unit cell of a lattice, including but are not limited to, rhombic dodecahedron, diamond, dodecahedron, square, pentagonal, hexagonal, octagonal, sctet struts, trunic octa, diagonal struts, other known geometric structures, and rounded, reinforced, weakened, or simplified versions of each geometry.

Lattices may also be included in implants as a structural component or a nonstructural component. Lattices used in structural applications are referred to herein as structural lattices, load-bearing lattices or stressed lattices. Repeating geometric shaped unit cells, particularly the rhombic dodecahedron, are well suited for use in structural lattices because of their strength to weight ratio. In structural lattice applications, the strength and elastic modulus of the lattice can be approximated by the volumetric density. When the volumetric density increases, the strength and the elastic modulus increases.

When configured to provide support for bone or tissue growth, a lattice can be referred to as a scaffold. Lattices are generally configured as scaffolds by controlling the size of the openings and interconnections disposed within the three-dimensional material. A scaffold, if used on the surface of an implant, may provide an osteointegration surface that allows adjacent bone to attach to the implant. A scaffold may also be configured to provide a path that allows bone to grow further than a mere surface attachment. Scaffolds intended for surface attachment are referred to herein as surface scaffolds. A surface scaffold may be one or more unit cells deep, but does not extend throughout the volume of an implant. Scaffolds intended to support ingrowth beyond mere surface attachment are referred to herein as bulk scaffolds.

A related structure to a lattice is a closed cell material. A closed cell material is similar to a lattice, in that it has openings contained within the bounds of a three-dimensional material, however, closed cell materials generally lack interconnections between openings. A closed cell structure may be accomplished using multiple methods, including the filling of certain cells or through the use of solid walls between the struts of unit cells. A closed cell structure can also be referred to as a cellular structure. It is possible to have a material that is a lattice in one portion and a closed cell material in another. It is also possible to have a closed cell material that is a lattice with respect to only certain interconnections between openings or vice versa. While the focus of the present disclosure is on lattices, the structures and methods disclosed herein can be easily adapted for use on closed cell structures within the inventive concept.

The lattice used in the present invention can be produced from a range of materials and processes. When used as a scaffold for bone growth, it is desirable for the lattice to be made of a biocompatible material that allows for bone attachment, either to the material directly or through the application of a bioactive surface treatment. In one example, the scaffold is comprised of an implantable metal. Implantable metals include, but are not limited to, zirconium, stainless steel (316 & 316L), tantalum, nitinol, cobalt chromium alloys, titanium and tungsten, and alloys thereof. Scaffolds comprised of an implantable metal may be produced using an additive metal fabrication or 3D printing process. Appropriate production processes include, but are not limited to, direct metal laser sintering, selective laser sintering, selective laser melting, electron beam melting, laminated object manufacturing and directed energy deposition. The material used in the body of the device may be different from that which is used in the endplates.

In another example, the lattice of the present invention is comprised of an implantable metal with a bioactive coating. Bioactive coatings include, but are not limited to, coatings to accelerate bone growth, anti-thrombogenic coatings, anti-microbial coatings, hydrophobic or hydrophilic coatings, and hemophobic, superhemophobic, or hemophilic coatings. Coatings that accelerate bone growth include, but are not limited to, calcium phosphate, hydroxyapatite ("HA"), silicate glass, stem cell derivatives, bone morphogenic proteins, titanium plasma spray, titanium beads and titanium mesh. Anti-thrombogenic coatings include, but are not limited to, low molecular weight fluoro-oligomers. Anti-microbial coatings include, but are not limited to, silver, organosilane compounds, iodine and silicon-nitride. Superhemophobic coatings include fluorinated nanotubes.

In another example, the lattice is made from a titanium alloy with an optional bioactive coating. In particular, Ti6A14V ELI wrought (American Society for Testing and Materials ("ASTM") F136) is a particularly well-suited titanium alloy for scaffolds. While Ti6A14V ELI wrought is the industry standard titanium alloy used for medical purposes, other titanium alloys, including but not limited to, unalloyed titanium (ASTM F67), Ti6A14V standard grade (ASTM F1472), Ti6A17Nb wrought (ASTM 1295), Ti5Al2.5Fe wrought (British Standards Association/International Standard Organization Part 10), CP and Ti6A14V standard grade powders (ASTM F1580), Ti13Nb13Zr wrought (ASTM F1713), the lower modulus Ti-24Nb-4Zr-8Sn and Ti12Mo6Zr2Fe wrought (ASTM F1813) can be appropriate for various embodiments of the present invention.

Titanium alloys are an appropriate material for scaffolds because they are biocompatible and allow for bone attachment. Various surface treatments can be done to titanium alloys to increase or decrease the level of bone attachment. Bone will attach to even polished titanium, but titanium with a surface texture allows for greater bone attachment. Methods of increasing bone attachment to titanium may be produced through a forging or milling process, sandblasting, RBM texturing, acid etching, and the use of a bioactive coating. Titanium parts produced with an additive metal fabrication or 3D printing process, such as direct metal laser sintering, can be treated with an acid bath to reduce surface stress risers, normalize surface topography, and improve surface oxide layer, while maintaining surface roughness and porosity to promote bone attachment.

Additionally, Titanium or other alloys may be treated with heparin, heparin sulfate (HS), glycosaminoglycans (GAG), chondroitin-4-sulphate (C4S), chondroitin-6-sulphate (C6S), hyaluronan (HY), and other proteoglycans with or without an aqueous calcium solution. Such treatment may occur while the material is in its pre-manufacturing form (often powder) or subsequent to manufacture of the structure.

While a range of structures, materials, surface treatments and coatings have been described, it is believed that a lattice using a repeating rhombic dodecahedron (hereinafter "RDD") unit cell can present a preferable combination of stiffness, strength, fatigue resistance, and conditions for bone ingrowth. In some embodiments, the repeating RDD lattice is comprised of titanium or a titanium alloy. Some embodiments include a repeating RDD unit cell with comprised of 24 struts that meet in 14 vertices, where the 24 struts define the 12 planar faces of the structure, where each face is an identical rhombus with an acute angle of 70.5 degrees and an obtuse angle of 109.5 degrees and disposed at the center of each planar face is an opening, or interconnection, allowing communication from inside the unit cell to outside the unit cell. At the center of some RDD unit cells is a generally spherical opening, the central void. Therefore, each RDD unit cell can have a central void and 12 interconnections to an area outside of the unit cell. When placed towards the center of a lattice structure, the 12 interconnections of an RDD unit cell can connect to 12 different adjacent unit cells, providing a continuous path through the lattice.

In some embodiments, the unit cell can be elongated in one or more directions to provide a lattice with anisotropic properties. When a unit cell is elongated, it generally reduces the elastic modulus in a direction normal to the direction of the elongation. The elastic modulus in the direction of the elongation is increased. It is desirable to elongate cells in the direction normal to the direction of new bone growth contained within the interconnections, openings and central voids (if any). By elongating the cells in a direction normal to the desired direction of reduced elastic modulus, the shear strength in the direction of the elongation may be increased, providing a desirable set of qualities when designing a structural scaffold. Covarying the overall stiffness of the scaffold may augment or diminish this effect, allowing variation in one or more directions.

In FIG. 1 is an isometric view of a first exemplary embodiment of a PLIF/TLIF implant 10 with an independent endplate structure. The PLIF/TLIF implant 10 can be inserted between the endplates of two adjacent vertebrae, providing mechanical spacing between the endplates of the adjacent vertebrae and mechanical stability to promote bone growth, allowing the vertebrae to fuse together over time.

The PLIF/TLIF implant 10 could be described as a PLIF or TLIF implant because PLIF and TLIF implants are often very similar and sometimes indistinguishable. Compared to PLIF implants, TLIF implants may be slightly longer (front to back) and may have a curve in a lateral direction. PLIF implants are generally implanted from a straight posterior approach, where TLIF implants are generally implanted from an angle between the posterior direction and a lateral direction. Both PLIF and TLIF implants may have lordosis. While the interbody fusion device 10 is described primarily as a PLIF implant, it could also be used in a TLIF procedure without change or with common features in some TLIF implants added.

The PLIF/TLIF implant 10 can be comprised substantially of three components—an upper endplate 11, a lower endplate 12 and a body 13. The upper and lower endplates 11 and 12 can be comprised of a biocompatible material with a higher elastic modulus in the superior to inferior direction than the body 13. The body 13 can be comprised of a biocompatible material with a lower elastic modulus in the superior to inferior direction than the upper and lower endplates 11 and 12.

The upper endplate 11 and lower endplate 12 are independent to one another with respect to their ability to move independently of one another. Independent, as used herein, refers to the ability of surfaces or volumes to move relative to another rather than refer to the lack of a physical connection. For instance, by attaching the upper endplate 11 and lower endplate 12 on opposite sides of a body 13, the endplates 11 & 12 can move independently of one another where the amount of independent movement can be determined largely by the elastic modulus of the body 13. While a body is disclosed as a structure that can provide independence between endplates, other structures may provide a similar independence. Other structures include, but are not limited to, a spring member between the endplates or any other mechanism that provides a different elastic modulus than the endplates themselves.

The body 13 preferably provides mechanical spacing between the adjacent vertebrae and provides adequate rigidity between the vertebrae to allow for bone ingrowth. The use of a body 13 with a lower elastic modulus than the endplates 11 and 12 can allow the new bone growth to be stressed while ingrowth occurs, resulting in a stronger fused bone. The relatively higher stiffness of the endplates 11 and 12 distributes the load across the surface of the less stiff body 13 and reduces the occurrence of the vertebral endplates from indenting the upper or lower surface of the body 13. In some examples, the endplates 11 and 12 use optional raised ridges or teeth 20 to mechanically anchor the endplates 11 and 12 to the endplates of the adjacent vertebrae. The ridges 20 extend from the endplates 11 and 12 to the surface of the body 13 that extends to the superior and inferior surface of the device. In addition to distributing the load across the body 13 and anchoring the interbody fusion device 10 relative to the adjacent vertebrae, the endplates 11 and 12 can allow for bone attachment, providing stability between the interbody fusion device and the endplates of the adjacent vertebrae.

The PLIF/TLIF implant 10 also provides an optional lumen 14 as a vertical bone fusion window and an optional viewing window 15 for radiolucency or bone fusion. The fusion or viewing windows can be used by clinicians to insert one or more compounds that promote bone growth or to assess fusion through the lumen 14 during the healing process. Some compounds that would be appropriate for use in the fusion or viewing windows 14 and 15 are autograft, allograft synthetic graft, or a combination.

The lower endplate 12 of the PLIF/TLIF implant 10 can include a substantially rigid section 16 to allow surgical tools to be fastened to the device 10 during a surgical procedure. In some examples, the rigid section 16 contains a threaded opening 17 that is configured to accept a threaded rod to facilitate placement of the device 10. On either side of the threaded opening 17 can be a void 21 designed to accommodate stabilizers on the threaded rod, if used. While the threaded opening 17 can provide an adequate amount of leverage to locate the device 10, the addition of two stabilizers on an installation instrument that contact the device 10 in the voids 21 can increase the ability of a surgeon to rotate the device during insertion. The rigid section 16 can be connected to the lower endplate 12 by a right connection arm 18 and left connection arm 19. In one example, the rigid section 16, right connection arm 18, left connection arm 19 and lower endplate 12 are comprised of a single piece of material. It is appreciated that various configurations could be used to accomplish the same ends. In some embodiments, the rigid section 16 is not attached directly to either the upper endplate 11 or lower endplate 12.

The upper and lower endplates 11 and 12 can be made of a biocompatible material that allows for bone attachment, either to the material directly or through the application of a bioactive surface treatment. In one embodiment, the upper and lower endplates 11 and 12 are made of an implantable metal. In another example, the upper and lower endplates 11 and 12 are made from titanium or an alloy thereof, providing strength to the endplates, with an optional bioactive coating. In another example, the upper and lower endplates 11 and 12 are made from commercially pure titanium, providing strength to the endplates, with an optional bioactive coating.

It is also contemplated that the upper and lower endplates 11 & 12 may be comprised of a lattice or scaffold structure to allow for bone ingrowth, while maintaining the ability of the endplates to sustain high point loads. If the upper and/or lower endplates 11 & 12 are comprised of a lattice or scaffold structure, they may be defined by their volumetric density. The volumetric density of an upper or lower endplate 11 & 12 is based on the volume of the endplate itself, not including the volume of the lumen within the endplate. In some embodiments, the upper and lower endplates 11 & 12 are comprised of a scaffold comprised of titanium or any alloys thereof with a volumetric density between and including 60% and 100%. In one example, the upper and lower endplates 11 and 12 are comprised of a scaffold comprised of titanium or any alloys thereof with a volumetric density between and including 80% and 100%. In another example, the endplates 11 & 12 are comprised of a scaffold comprised of titanium or any alloys thereof with a volumetric density between and including 70% and 90%. In another example, the endplates 11 & 12 are comprised of a scaffold comprised of titanium or any alloys thereof with a volumetric density between and including 60% and 64%. In some embodiments, the endplates 11 & 12 are comprised of a scaffold comprised of titanium or any alloys thereof with a volumetric density of less than 60%.

The volumetric density and material chosen for the endplates 11 & 12 can be varied to achieve an endplate with an elastic modulus that is indexed to the elastic modulus of the body. In some embodiments, the elastic modulus of the endplates is selected based on the stiffness of the adjacent bone. In most patients, cortical bone has an elastic modulus between and including 15.2 to 20.7 GPa. When selecting an elastic modulus for the endplates 11 & 12, a patient's actual cortical bone elastic modulus may be used or an approximation based on the patient's age and medical history may be used. In some embodiments, the elastic modulus of the endplates 11 & 12 can be less than the elastic modulus of the patient's cortical layer of bone. In certain surgical procedures, portions of a patient's cortical bone at the implant site may be removed, making it beneficial to reduce the elastic modulus of the endplates 11 & 12 below that of cancellous bone. In some embodiments, it may be desirable for the endplates to have an elastic modulus that is less than that of the patient's cancellous bone.

In some embodiments, the upper and lower endplates 11 & 12 are comprised of a lattice with an elastic modulus between and including 10 MPa to 130 GPa. Embodiments of the device include examples where the upper and lower endplates are comprised of a lattice with an elastic modulus between and including 10 MPa to 5 GPa, 300 MPa to 5 GPa, 1 GPa to 5 GPa, 5 GPa to 10 GPa, 10 GPa to 15 GPa., 15 GPa to 21 GPa and 21 GPa to 130 GPa. In some examples, the lattice is comprised of a metallic scaffold. In others, the lattice is comprised of a scaffold comprised of titanium or any alloys thereof. In this embodiment and others, the use of endplates or a body with a lower modulus of elasticity, within the ranges given, could be beneficial for use in patients with poor bone quality or who are osteoperotic.

In some embodiments, the upper endplate 11 and lower endplate 12 are comprised of the same material and possess the same volumetric density and lattice structure. In other embodiments, the upper endplate 11 and lower endplate 12 are comprised of different materials, volumetric density and/or lattice structure. It could be desirable for the upper endplate 11 and lower endplate 12 to have different physical properties when the strength and composition of the adjacent bone is different near their respective endplate.

In one example, the body 13 is comprised of an implantable material that provides a scaffold for bone growth. In another example, the body 13 is comprised of titanium or any alloys thereof, with an optional bioactive coating. In another example, the body 13 is made from commercially pure titanium, with an optional bioactive coating. The body 13 is preferably comprised of a structural lattice to provide mechanical separation between the endplates 11 & 12. The body 13 is more preferably comprised of a repeating RDD structural scaffold comprised of titanium or any alloys thereof with a volumetric density between and including 5% to 50%. In some embodiments, the body 13 is comprised of a repeating RDD structural scaffold comprised of titanium or any alloys thereof with a volumetric density between and including 5% to 10%. In some embodiments with a body with a lower modulus of elasticity, the body 13 is comprised of a repeating RDD structural scaffold comprised of titanium or any alloys thereof with a volumetric density between and including 10% to 18%. In some embodiments, the body 13 is comprised of a repeating RDD structural scaffold comprised of titanium or any alloys thereof with a volumetric density between and including 18% to 25%. In some embodiments, the body 13 is comprised of a repeating RDD structural scaffold comprised of titanium or any alloys thereof with a volumetric density between and including 25% to 35%. In some embodiments, the body 13 is comprised of a repeating RDD structural scaffold comprised of titanium or any alloys thereof with a volumetric density between and including 35% to 50%. The preferred volumetric density ranges disclosed are directed towards a body 13 constructed from a repeating RDD structural scaffold comprised of titanium or any alloys thereof and can be adjusted within the scope of the inventive concept to suit a different material or different lattice structure.

In one example, the body 13 is comprised of a lattice comprised of titanium or any alloys thereof with an elastic modulus in the superior to inferior direction of between and including 8 to 12 GPa. In another example, the body 13 is comprised of a lattice comprised of titanium or any alloys thereof with an elastic modulus in the superior to inferior direction of between and including 1 to 5 GPa. In another example, the body 13 is comprised of a lattice comprised of titanium or any alloys thereof with an elastic modulus in the superior to inferior direction of between and including 2 to 4 GPa. In another example, the body 13 is comprised of a lattice comprised of titanium or any alloys thereof with an elastic modulus in the superior to inferior direction of between and including 3 to 9 GPa. In another example, the body 13 is comprised of a lattice comprised of titanium or any alloys thereof with an elastic modulus in the superior to inferior direction of between and including 10 MPa to 300 MPa. In another example, the body 13 is comprised of a lattice comprised of titanium or any alloys thereof with an elastic modulus in the superior to inferior direction of between and including 300 MPa to 2 GPa. In another example, the body 13 is comprised of a lattice comprised of titanium or any alloys thereof with an elastic modulus in the superior to inferior direction of between and including 300 MPa to 4 GPa. In another example, the body 13 is comprised of a lattice comprised of titanium or any alloys thereof with an elastic modulus in the superior to inferior direction that is substantially similar to the bulk elastic modulus in the superior to inferior direction of the adjacent bone.

To achieve a targeted elastic modulus in the superior to inferior direction, the shape of the lattice structure and/or the volumetric density of the body 13 can be adjusted to suit a particular material and material's elastic modulus. While any implantable material could be used for the body 13, the shape of the lattice structure and volumetric density of the material may need to be changed to create a body 13 with the specific elastic modulus required. For instance, a material with a lower elastic modulus than a titanium alloy when both have a volumetric density of 100% would need to have a higher volumetric density or use a lattice repeating unit cell shape that increases the elastic modulus of the structure to achieve a body with a similar elastic modulus.

By adapting the lattice structure and volumetric density of the material, any implantable material could be appropriate for the body 13. In one example, the body 13 is comprised of an implantable lattice with an elastic modulus in the superior to inferior direction of between 8 to 12 GPa. In another example, the body 13 is comprised of an implantable lattice with an elastic modulus in the superior to inferior direction of between 1 to 5 GPa. In another example, the body 13 is comprised of an implantable lattice with an elastic modulus in the superior to inferior direction of between 2 to 4 GPa. In another example, the body 13 is comprised of an implantable lattice with an elastic modulus in the superior to inferior direction of between 3 to 9 GPa. In another example, the body 13 is comprised of an implantable lattice with an elastic modulus in the superior to inferior direction of between and including 10 MPa to 300 MPa. In another example, the body 13 is comprised of an implantable lattice with an elastic modulus in the superior to inferior direction of between and including 300 MPa to 2 GPa. In another example, the body 13 is comprised of an implantable lattice with an elastic modulus in the superior to inferior direction of between and including 300 MPa to 4 GPa. In another example, the body 13 is comprised of an implantable lattice with an elastic modulus in the superior to inferior direction that is substantially similar to the bulk elastic modulus in the superior to inferior direction of the adjacent bone. While implantable metals are often an appropriate material for the body 13, other materials with a similar elastic modulus and/or the capacity for bone ingrowth can also be used, including, but are not limited to, a glass ceramic composition with a porous structure.

The body 13 may optionally be treated with one or more bioactive coatings in one or more areas to promote certain reactions. For instance, the body 13 may optionally be treated with a bioactive coating, such as an HA coating, to promote bone growth.

The volumetric density of the body 13 may also be varied to adjust the mechanical stability offered by the device 10 in a particular direction. In one example, the body 13 has a higher elastic modulus at the front and back of the device 10. In one example, the area between the back of the device and the back wall of the lumen 14 and the area between the front of the device and the front wall of the lumen 14 have an elastic modulus between and including 8 to 12 GPa and the remainder of the body has an elastic modulus between and including 4 to 8 GPa. In some examples, it may be desirable for the body 13 to have a higher elastic modulus at the center of the device than towards the front and back. A lower elastic modulus towards the edges of a device could reduce stress risers in the vertebral endplate, especially if the edges of the implant have a high risk of subsidence into the vertebral endplate or the implant is too small for the disc space. The use of a lower modulus of elasticity towards the center of a device would allow less pressure on the softer center of the vertebral endplate, which would be beneficial in patients with low bone quality so that the implant edges can rest on the stronger annulus of the vertebral body. The elastic modulus of the body may be adjusted by varying the parameters of the body 13. When the body 13 is a repeating geometric metallic lattice, the parameters of the unit cells may be locally modified to change the elastic modulus of that area. Some methods of increasing the strength and elastic modulus include, but are not limited to, increasing the diameter of the unit cell struts, increasing the size of the unit cell nodes, applying post-processing such as HIP treatment to unify material grains, modifying laser printing characteristics to control layer adhesion strength, or applying etching processes to reduce crack propagation sites. Performing the opposite modification would generally decrease the elastic modulus.

The lumen 14 and window 15 can optionally be filled with a lattice or scaffold of substantially the same material as the body 13. The lumen 14 and window 15 could also be optionally be filled with a lattice or scaffold with a different volumetric density, primary material and/or unit cell structure than the body 13 to affect the bone ingrowth process.

Figure 2:
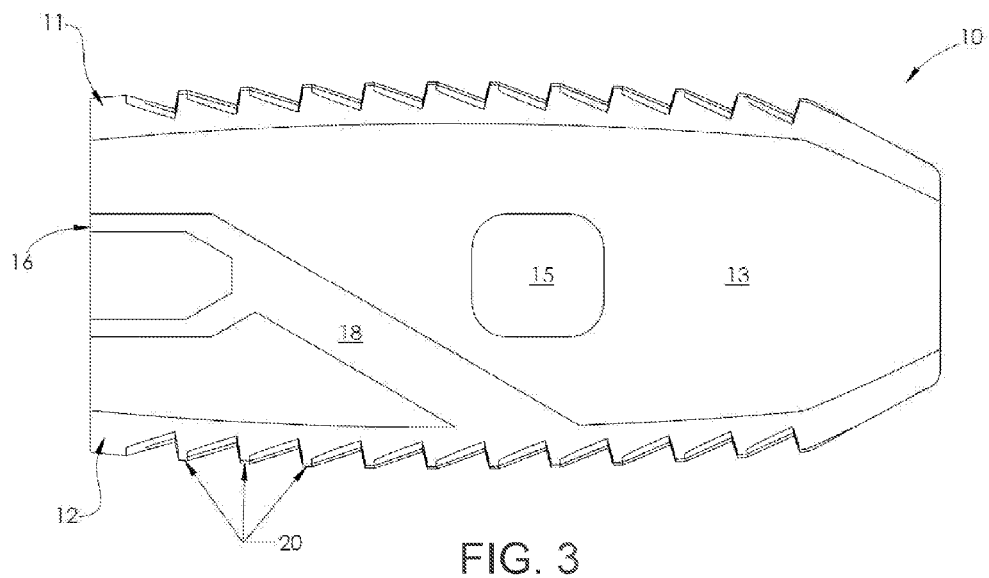
FIG. 2 is a right-side view of a PLIF/TLIF implant showing a separation between the endplates.

In FIG. 2 is a right-side view of the PLIF/TLIF implant 10. In some versions, the left side view is a mirror image of the right-side view. In some versions, the left side and right-side may not be a mirror image. From the side, the upper endplate 11, lower endplate 12 and body 13 are visible. The ridges 20 are present on the superior and inferior surface of the device 10 on the upper and lower endplates 11 and 12 and the portion of the body 13 that extends to the superior and inferior surfaces. The ridges 20 can be changed depending on the particular application and it is appreciated that many different types of ridges or surface patterns could be used to provide mechanical stabilization of the device 10 relative to the endplates of the adjacent vertebrae.

The window 15 is visible from the side and extends through the device in some examples. While this example shows a square opening with rounded corners and substantially the same shape through the device, other fusion window shapes could be used effectively. The rigid section 16 can be formed as a single piece, including the right connection arm 18, left connection arm 19 (not visible in this view) and the lower endplate 12. The left connection arm 19 can be substantially the same shape as the right connection arm 18.

Figure 3:
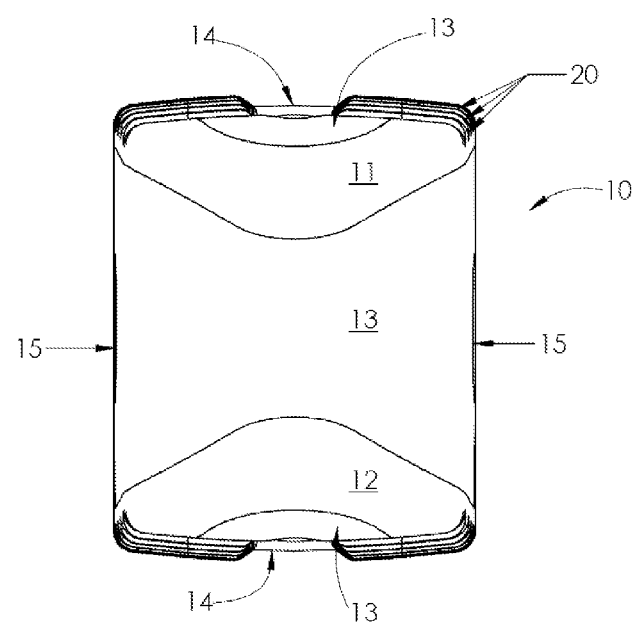
FIG. 3 is a front view of a PLIF/TLIF implant showing the leading edge of the implant and the separation between the endplates.

In FIG. 3 is a front view of the interbody fusion device 10. From the front, the upper endplate 11, lower endplate 12 and body 13 are visible. The upper and lower endplates 11 and 12 can taper together towards the front of the device. Because of the taper, the portions of the body that extends to the superior and inferior surfaces are visible in this view. The sides of the device 10 also taper towards the front of the device so that the openings to window 15 are visible from the front. The openings for the lumen 14 are also visible from the front, adjacent to the ridges 20.

Figure 4:
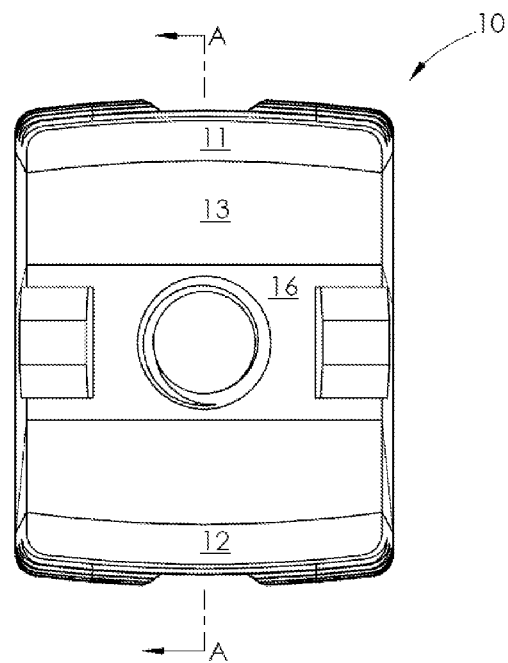
FIG. 4 is a rear view of a PLIF/TLIF implant showing an optional tool engagement area.

In FIG. 4 is a rear view of the PLIF/TLIF implant 10. From the rear, the upper endplate 11, lower endplate 12 and body 13 are visible. Rigid section 16 can face rearward to assist in placing the device in a patient. The location of rigid section 16 can vary based on the location where the device is to be inserted. In FIG. 4, the line between the points labeled "A" define the section view of FIG. 5.

Figure 5:
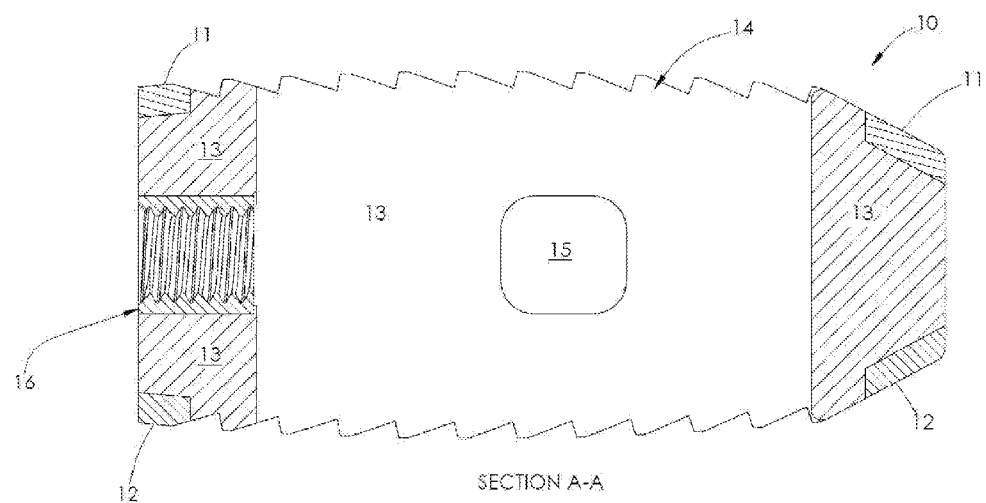
FIG. 5 is a side sectioned view, sectioned at plane defined by line AA in FIG. 4, of a PLIF/TLIF implant showing the separation between the endplates throughout the device.

In FIG. 5 is a side sectioned view of the first exemplary embodiment of the interbody fusion device 10. In the sectioned view of FIG. 5, the device is shown from the right side where the device was cut vertically along the centerline of the device (along line AA) if viewed from the front or rear.

The sectioned view of FIG. 5 cuts through the upper endplate 11, lower endplate 12, the body 13 and the rigid section 16. In this example, the upper endplate 11 is connected to the top of the body 13 and the lower endplate is connected to the bottom of the body 13, without a direct connection between the upper endplate 11 and lower endplate 13. The lack of a direct and rigid connection between the upper endplate 11 and lower endplate 12 allow them to move independently of one another, largely based on the physical properties of the body 13. Without a rigid connection between the endplates 11 & 12, this example allows the physical properties of the body 13 to largely dictate the level of mechanical stability afforded to the adjacent vertebrae. There may be direct connections between the endplates 11 &

12 to adjust the construct properties as long as the endplates 11 & 12 are capable of movement independent of one another.

As noted earlier, other structures can be employed to allow independence between the endplates 11 & 12, including but not limited to, springs or member(s) that allow the endplates 11 & 12 to move relative to one another. In some embodiments, the body can be substituted with a structure that allows independence between the endplates 11 & 12. In some embodiments, the volumetric density of the endplates is higher than that of the body, causing the body's properties to substantially dominate the properties of the implant.

In FIG. 5, the lumen 14 is sectioned through its center in this view so that the left wall of the lumen 14 is visible. In this example, the window 15 passes through both sides of the body 13 and the portion passing through the left side of the device 10 is visible. The rigid section 16 can be connected to the lower endplate 12 by right and left connection arms 18 and 19 that are not visible in this view. The connection arms, in this example, run along the exterior sides of the device 10, but do not extend to the vertical fusion window 14.

Figure 6:
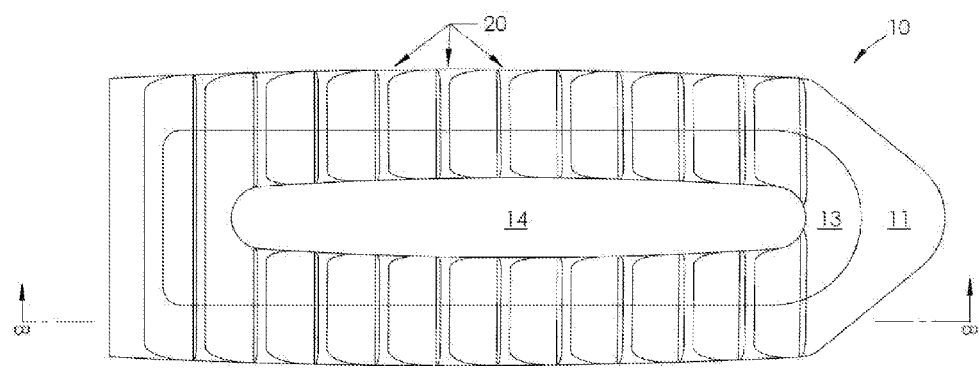
FIG. 6 is a top view of a PLIF/TLIF implant showing an exemplary configuration for an endplate surface.

In FIG. 6 is a top view of the first exemplary embodiment of the PLIF/TLIF implant 10. In some examples, the bottom view can be a mirror image of the top view, however in other examples, the top view and bottom view may not be a mirror image of one another. From the top, the upper endplate 11 and body 13 are visible. The orientation and shape of the lumen 14 can be clearly seen in this view. While the lumen 14 is shown as an oval shaped opening of the same size in the superior to inferior direction, other shapes could be appropriate for the lumen. In this example, the portion of the body 13 that extends to the superior surface is flush with the superior surface of the upper endplate 11 so that the ridges 20 of the upper endplate 11 extend to the surface of the body 13. In FIG. 6, the line between the points labeled "B" define the section view of FIG. 7.

Figure 7:
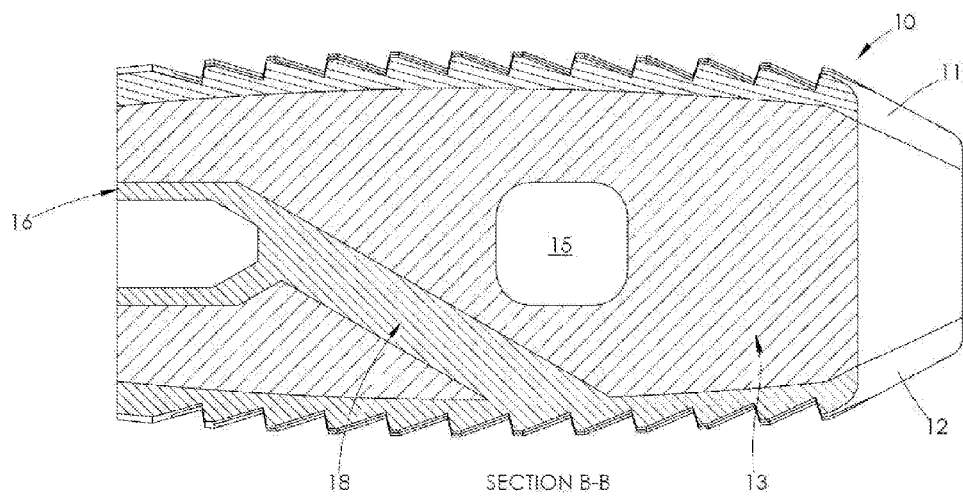
FIG. 7 is a side sectioned view, sectioned at a plane defined by line BB in FIG. 6, of a PLIF/TLIF implant also showing the separation between the endplates throughout the device.

In FIG. 7 is an alternative side sectioned view of the interbody fusion device 10. In the sectioned view of FIG. 7, the device is shown from the right side where the device was cut vertically to the right of the centerline of the device (along line BB) if viewed from the top or rear.

The sectioned view of FIG. 7 cuts through the upper endplate 11, lower endplate 12, the body 13, the rigid section 16 and the right connection arm 18. The section was taken to the right of centerline between the lumen 14 (not visible in this view) and the right side of the device 10. Also, clearly visible in this sectioned view is that the upper endplate 11 and lower endplate 12 are connected only to the body 13, without a direct and rigid connection between the endplates 11 & 12. As there is no direct and rigid connection between the endplates 11 & 12, the physical properties of the body 13 dictate the level of mechanical stability afforded to the adjacent vertebrae. There may be direct connections between the endplates 11 & 12 to adjust the construct properties as long as the endplates 11 & 12 are capable of movement independent of one another. In this example, the window 15 passes through both sides of the body 13 and the portion passing through the right side of the device 10 is visible. The right connection arm 18 that connects the rigid section 16 to the lower endplate 12 is sectioned in this view. Certain ranges of elastic moduli for the endplates 11 & 12 and the body 13 were disclosed above, but the use of endplates with an elastic modulus indexed from that of the body can provide the benefits of increased bone loading without surface deformations to the implant that can compromise the strength characteristics of the material. The elastic moduli ranges for the endplates and body can be narrowed and selected based on the tables and equations later in this disclosure.

In FIGS. 8 to 15 is an ALIF implant 130 with an independent endplate structure. The ALIF implant 130 can be inserted between the endplates of two adjacent vertebrae, providing mechanical spacing between the endplates of the adjacent vertebrae and mechanical stability to promote bone growth, allowing the vertebrae to fuse together over time. The ALIF implant 130 can be comprised substantially of three components—an upper endplate 111, a lower endplate 112 and a body 113. The upper and lower endplates 111 & 112 can be comprised of a biocompatible material with a higher elastic modulus in the superior to inferior direction than the body 113. The body 113 can be comprised of a biocompatible material with a lower elastic modulus in the superior to inferior direction than the upper and lower endplates 111 & 112.

Figure 8:
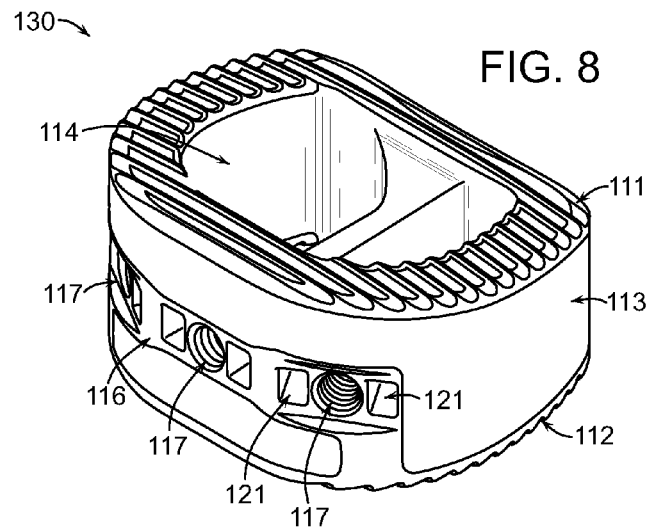
FIG. 8 is an isometric view of an anterior lumbar interbody fusion (hereinafter "ALIF") implant showing the inventive configuration of the endplates relative to the body on the exterior of the device.
Figure 9:
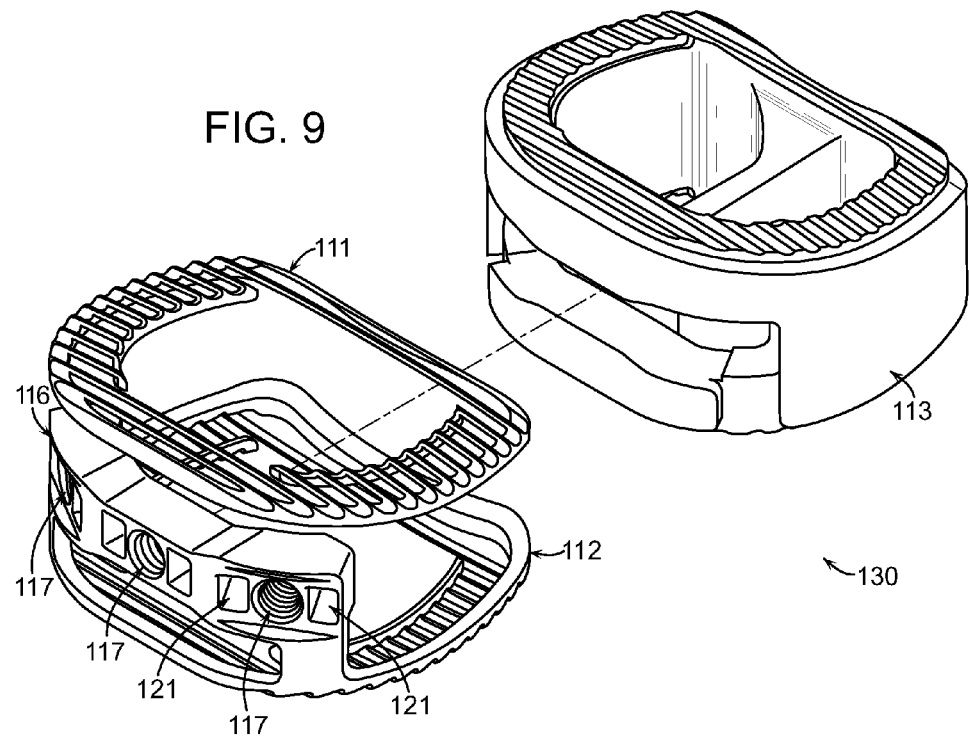
FIG. 9 is an exploded isometric view of an ALIF implant showing the endplates separated from the body.
Figure 10:
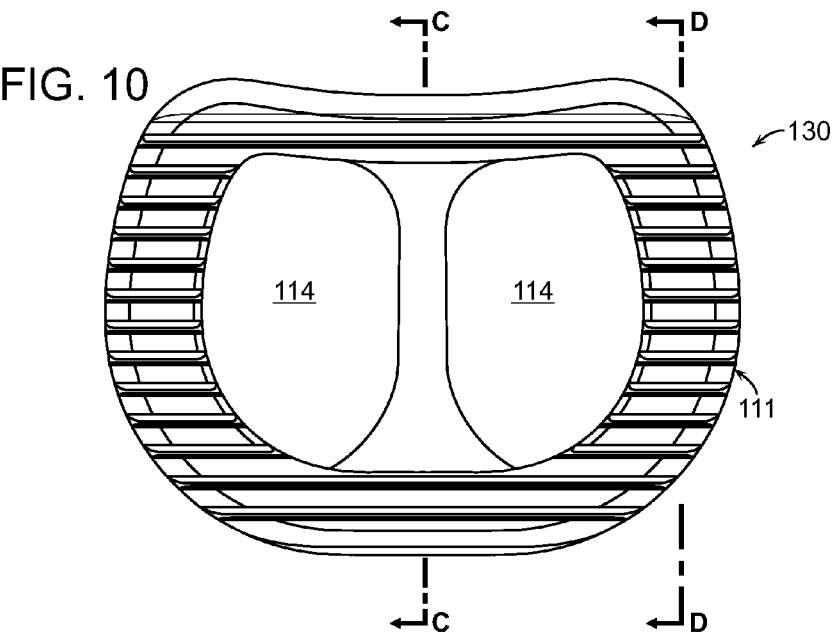
FIG. 10 is a top view of the ALIF implant showing a possible configuration of an endplate top surface and the location of later presented section views.
Figure 11:
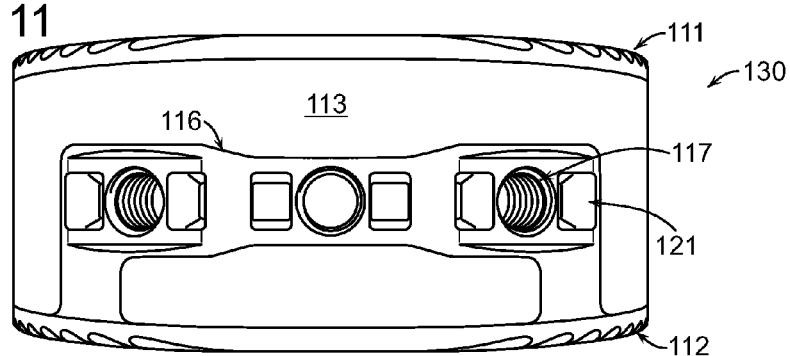
FIG. 11 is a rear view of the ALIF implant showing the optional rear tool engagement area.
Figure 12:
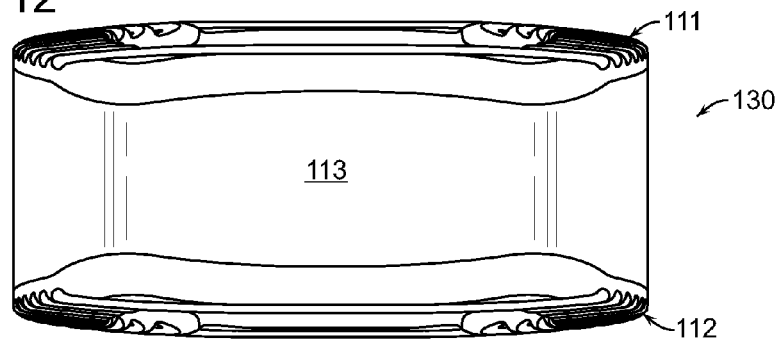
FIG. 12 is a front view of the ALIF implant showing the position of the endplates relative to one another.
Figure 13:
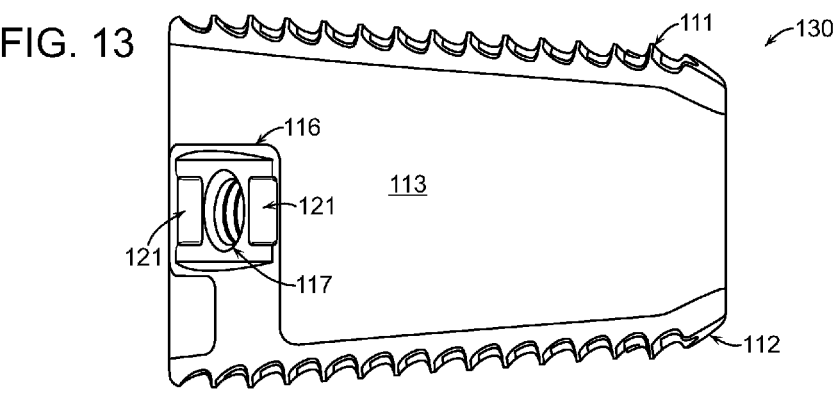
FIG. 13 is a side view of the ALIF implant also showing the position of the endplates relative to one another.
Figure 14:
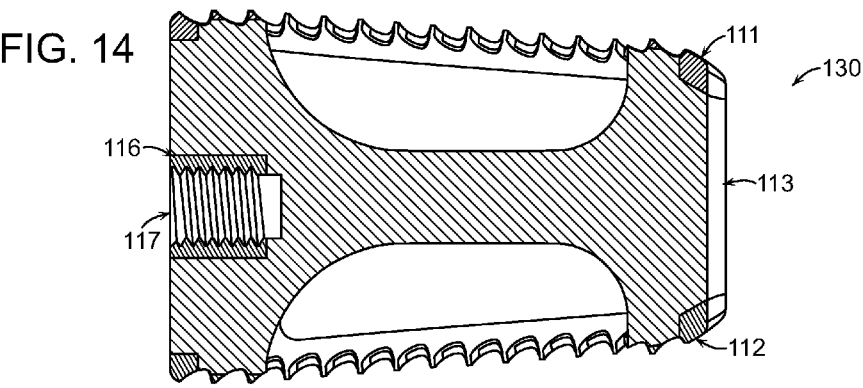
FIG. 14 is a side sectioned view of the ALIF implant, sectioned through line CC in FIG. 10.
Figure 15:
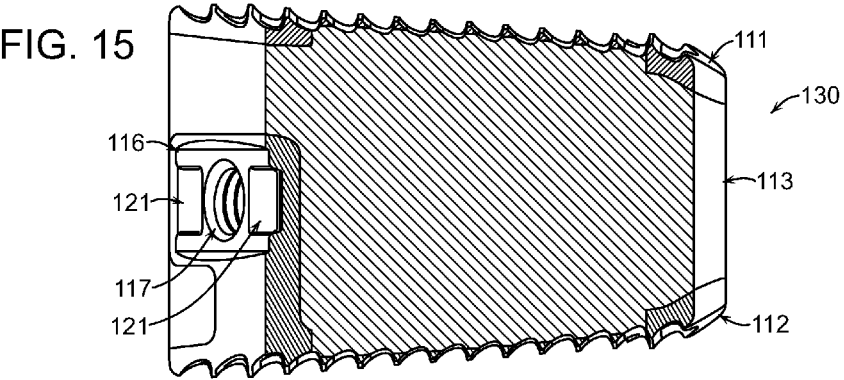
FIG. 15 is an alternative side sectioned view of the ALIF implant, sectioned through line DD in FIG. 10.

In FIG. 8 is an isometric view of the ALIF implant 130, showing the independent configuration of the endplates 111 & 112 relative to the body 113. In FIG. 9 is an exploded isometric view of the ALIF implant 130, showing the endplates 111 & 112 separated from the body 113, showing the lack of a direct and rigid connection between the endplates 111 & 112 in this embodiment. There may be direct connections between the endplates 111 & 112 to adjust the construct properties as long as the endplates 111 & 112 are capable of movement independent of one another. In FIG. 10 is a top view of the ALIF implant 130 showing an exemplary endplate configuration and identifying lines CC and DD. In FIG. 11 is a rear view of the ALIF implant 130 showing the optional rear tool engagement area. In FIG. 12 is a front view of the ALIF implant 130 showing the position of the endplates relative to one another. In FIG. 13 is a side view of the ALIF implant 130, also showing the position of the endplates relative to one another. In FIG. 14 is a side sectioned view of the ALIF implant 130, sectioned through line CC in FIG. 10 and in FIG. 14 is an alternative side sectioned view of the ALIF implant 130, sectioned through line DD in FIG. 10. The side sectioned views show that the endplates 111 & 112 do not directly contact one another throughout the device in this example.

The upper endplate 111 and lower endplate 112 are independent to one another with respect to their ability to move independently of one another. In some embodiments, the upper endplate 111 and lower endplate 112 are on opposite sides of the body 113 so that the endplates 111 & 112 can move independently of one another and where the amount of independent movement can be determined largely by the stiffness of the body 113. While a body is disclosed as a structure that can provide independence between endplates, other structures noted previously may provide a similar independence.

The body 113 preferably provides mechanical spacing between the adjacent vertebrae and provides adequate rigidity between the vertebrae to allow for bone ingrowth. The use of a body 113 with a lower elastic modulus than the endplates 111 & 112 can allow the new bone growth to be stressed while ingrowth occurs, resulting in a stronger fused bone. The relatively higher modulus of elasticity of the endplates 111 & 112 distributes the load across the surface of the body 113 and reduces the occurrence of the vertebral endplates from indenting the upper or lower surface of the body 113. In some examples, the endplates 111 & 112 use optional raised ridges or teeth 120 to mechanically anchor the endplates 111 & 112 to the endplates of the adjacent vertebrae. The ridges 120 can extend from the endplates 111

& 112 to the surface of the body 113 that extends to the superior and inferior surface of the device. In addition to distributing the load across the body 113 and anchoring the interbody fusion device 130 relative to the adjacent vertebrae, the endplates 111 & 112 can allow for bone attachment or ingrowth, providing stability between the interbody fusion device and the endplates of the adjacent vertebrae.

The interbody fusion device 130 also provides optional lumen 114 as vertical bone fusion windows for radiolucency or bone fusion. The fusion windows can be used by clinicians to insert one or more compounds that promote bone growth or to assess fusion through the lumen 114 during the healing process. Some compounds that would be appropriate for use in the fusion or viewing windows 114are autograft, allograft synthetic graft, or a combination.

The lower endplate 112 of the ALIF implant 130 can include a substantially rigid section 116 to allow surgical tools to be fastened to the device 130 during a surgical procedure. In some examples, the rigid section 116 contains one or more threaded openings 117 that are configured to accept a threaded rod to facilitate placement of the device 130. On either side of each threaded opening 117 can be a void 121 designed to accommodate stabilizers on the threaded rod, if used. While the threaded openings 117 can provide an adequate amount of leverage to locate the device 130, the addition of stabilizers on an installation instrument that contact the device 130 in the voids 121 can increase the ability of a surgeon to rotate the device during insertion. The rigid section 116 can be connected to an endplate 111 & 112 and/or to the body 113.

In some embodiments, the upper and lower endplates 111 & 112 are comprised of a lattice with a volumetric density between and including 60% and 100%. Embodiments of the device include examples where the endplates 111 & 112 are comprised of a lattice with a volumetric density between and including 80% and 100%, 70% and 90%, 60% and 64% and less than 60%. In some embodiments, the body 113 is comprised of a lattice with a volumetric density between and including 5% to 50%. Embodiments of the device include examples where the body 113 is comprised of a lattice with a volumetric density between and including 5% to 10%, 10% to 18%, 18% to 25%, 25% to 35% and 35% to 50%. In some examples, the lattice is comprised of a metallic scaffold. In others, the lattice is comprised of a scaffold comprised of titanium of an alloy thereof.

In some embodiments, the upper and lower endplates 111 & 112 are comprised of a lattice with an elastic modulus between and including 300 MPa to 130 GPa. Embodiments of the device include examples where the upper and lower endplates are comprised of a lattice with an elastic modulus between and including 300 MPa to 5 GPa, 1 GPa to 5 GPa, 5 GPa to 10 GPa, 10 GPa to 15 GPa., 15 GPa to 21 GPa and 21 GPa to 130 GPa. In some embodiments, the body 113 is comprised of a lattice with an elastic modulus between and including 10 MPa to 12 GPa. Embodiments of the device include examples where the body 113 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa and 8 GPa to 12 GPa. In another example, the body 113 is comprised of a lattice with an elastic modulus that is substantially similar to the bulk elastic modulus of the adjacent bone. In some examples, the lattice is comprised of a metallic scaffold. In others, the lattice is comprised of a scaffold comprised of titanium or an alloy thereof.

In FIGS. 16 to 23 is a second ALIF implant 230 with an independent endplate structure. The second ALIF implant 230 can be inserted between the endplates of two adjacent vertebrae, providing mechanical spacing between the endplates of the adjacent vertebrae and mechanical stability to promote bone growth, allowing the vertebrae to fuse together over time. The second ALIF implant 230 can be comprised substantially of three components—an upper endplate 211, a lower endplate 212 and a body 213. The upper and lower endplates 211 & 212 can be comprised of a biocompatible material with a higher elastic modulus in the superior to inferior direction than the body 213. The body 213 can be comprised of a biocompatible material with a lower elastic modulus in the superior to inferior direction than the upper and lower endplates 211 & 212.

Figure 16:
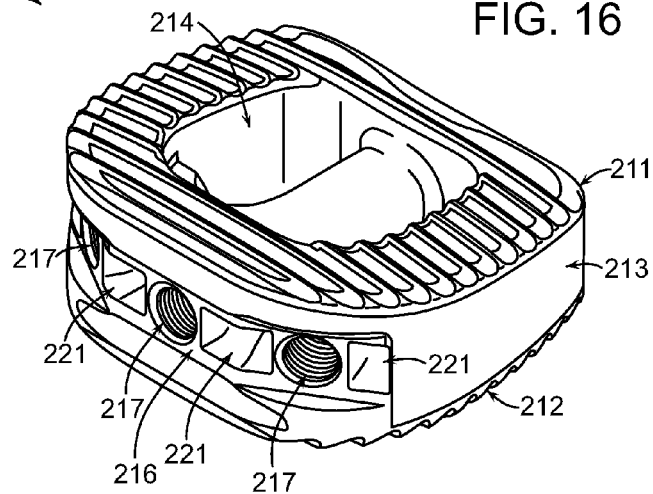
FIG. 16 is an isometric view of a second ALIF implant showing the inventive configuration of the endplates relative to the body on the exterior of the device.
Figure 17:
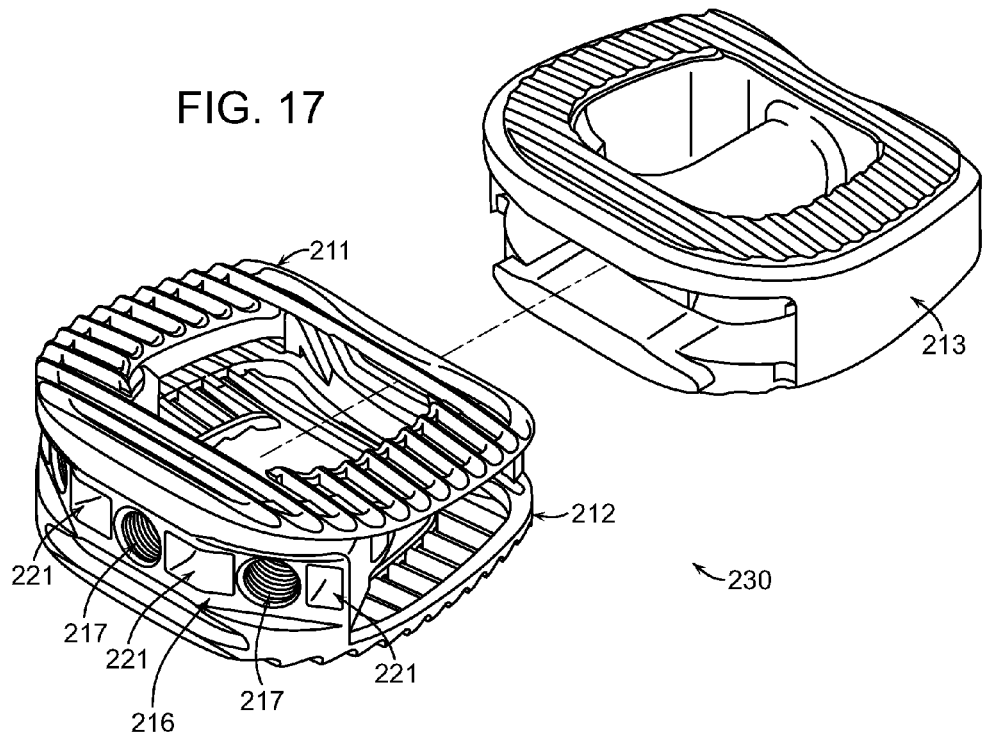
FIG. 17 is an exploded isometric view of the second ALIF implant showing the endplates separated from the body.
Figure 18:
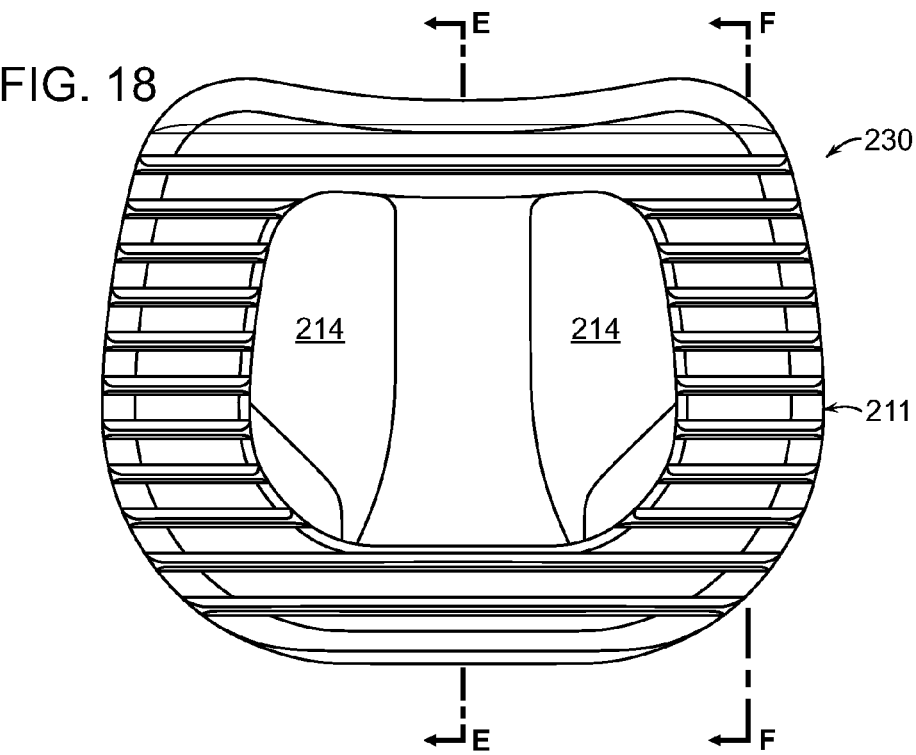
FIG. 18 is a top view of the second ALIF implant showing a possible configuration of an endplate top surface and the location of later presented section views.
Figure 19:
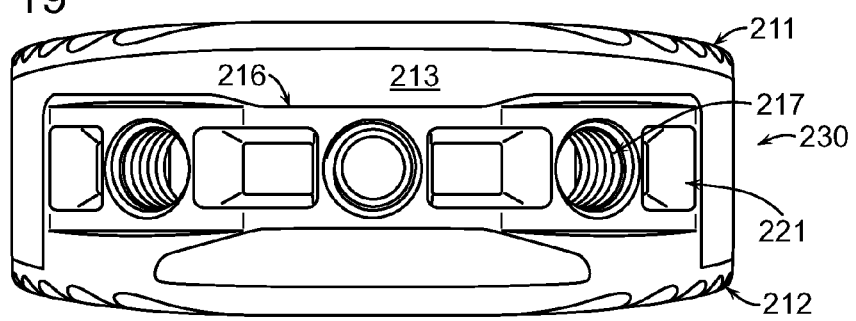
FIG. 19 is a rear view of the second ALIF implant showing the optional rear tool engagement area.
Figure 20:
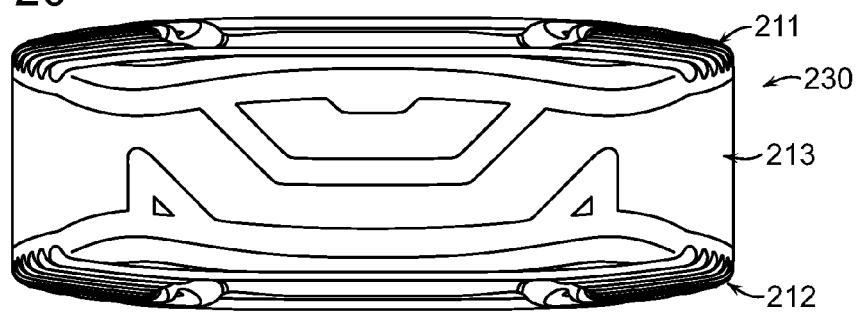
FIG. 20 is a front view of the second ALIF implant showing the position of the endplates relative to one another.
Figure 21:
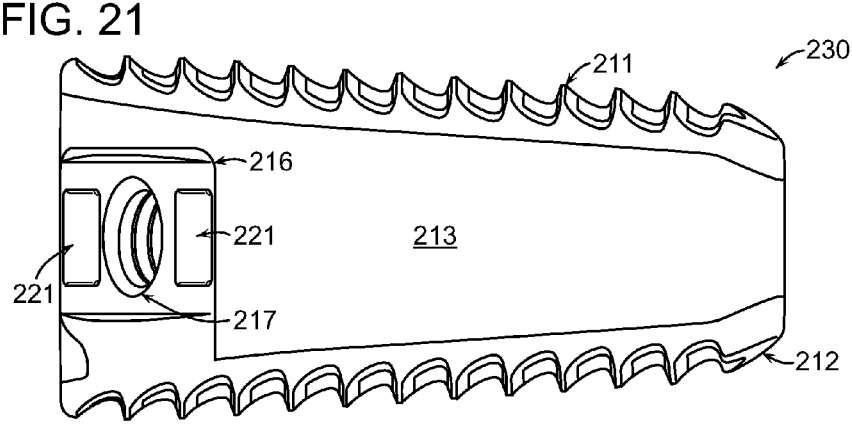
FIG. 21 is a side view of the second ALIF implant also showing the position of the endplates relative to one another.
Figure 22:
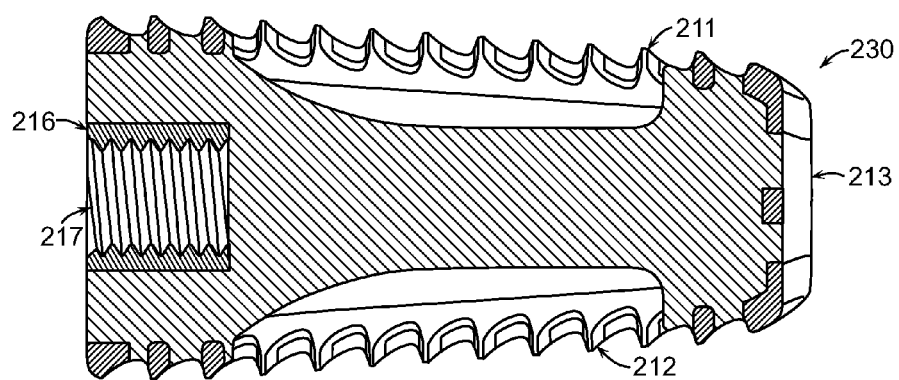
FIG. 22 is a side sectioned view of the second ALIF implant, sectioned through line EE in FIG. 18.
Figure 23:
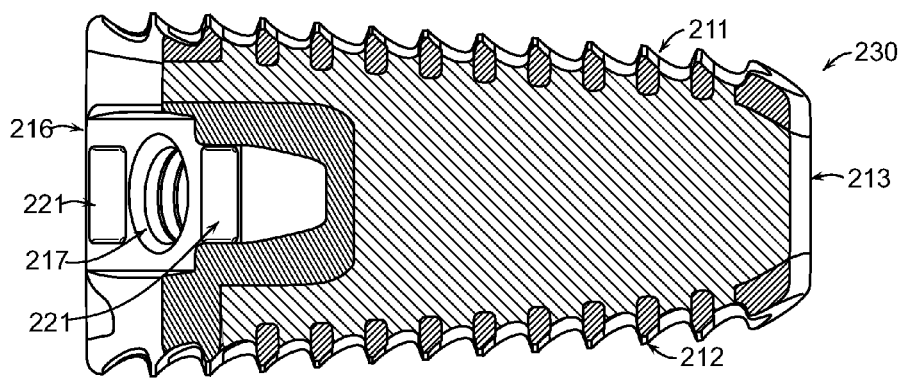
FIG. 23 is an alternative side sectioned view of the second ALIF implant, sectioned through line FF in FIG. 18.

In FIG. 16 is an isometric view of the second ALIF implant 230, showing the independent configuration of the endplates 211 & 212 relative to the body 213. In FIG. 17 is an exploded isometric view of the second ALIF implant 130, showing the endplates 211 & 212 separated from the body 213, showing the lack of a direct and rigid connection between the endplates 211 & 212 in this embodiment. There may be direct connections between the endplates 211 & 212 to adjust the construct properties as long as the endplates 211 & 212 are capable of movement independent of one another. In FIG. 18 is a top view of the second ALIF implant 230 showing an exemplary endplate configuration and identifying lines EE and FF. In FIG. 19 is a rear view of the second ALIF implant 230 showing the optional rear tool engagement area. In FIG. 20 is a front view of the second ALIF implant 230 showing the position of the endplates relative to one another. In FIG. 21 is a side view of the second ALIF implant 230, also showing the position of the endplates relative to one another. In FIG. 22 is a side sectioned view of the second ALIF implant 230, sectioned through line EE in FIG. 18 and in FIG. 23 is an alternative side sectioned view of the second ALIF implant 230, sectioned through line FF in FIG. 18. The side sectioned views show that the endplates 211 & 212 do not directly contact one another throughout the device in this example.

The upper endplate 211 and lower endplate 212 are independent to one another with respect to their ability to move independently of one another. In some embodiments, the upper endplate 211 and lower endplate 212 are on opposite sides of the body 213 so that the endplates 211 & 212 can move independently of one another and where the amount of independent movement can be determined largely by the stiffness of the body 213. While a body is disclosed as a structure that can provide independence between endplates, other structures noted previously may provide a similar independence.

The body 213 preferably provides mechanical spacing between the adjacent vertebrae and provides adequate rigidity between the vertebrae to allow for bone ingrowth. The use of a body 213 with a lower elastic modulus than the endplates 211 & 212 can allow the new bone growth to be stressed while ingrowth occurs, resulting in a stronger fused bone. The relatively higher modulus of elasticity of the endplates 211 & 212 distributes the load across the surface of the body 213 and reduces the occurrence of the vertebral endplates from indenting the upper or lower surface of the body 213. In some examples, the endplates 211 & 212 use optional raised ridges or teeth 220 to mechanically anchor the endplates 211 & 212 to the endplates of the adjacent vertebrae. The ridges 220 can extend from the endplates 211 & 212 to the surface of the body 213 that extends to the superior and inferior surface of the device. In addition to distributing the load across the body 213 and anchoring the interbody fusion device 230 relative to the adjacent vertebrae, the endplates 211 & 212 can allow for bone attachment or ingrowth, providing stability between the interbody fusion device and the endplates of the adjacent vertebrae.

The interbody fusion device 230 also provides optional lumen 214 as vertical bone fusion windows for radiolucency or bone fusion. The fusion windows can be used by clinicians to insert one or more compounds that promote bone growth or to assess fusion through the lumen 214 during the healing process. Some compounds that would be appropriate for use in the fusion or viewing windows 214 and 215 are autograft, allograft synthetic graft, or a combination.

The lower endplate 212 of the ALIF implant 230 can include a substantially rigid section 216 to allow surgical tools to be fastened to the device 230 during a surgical procedure. In some examples, the rigid section 216 contains one or more threaded openings 217 that are configured to accept a threaded rod to facilitate placement of the device 230. On either side of each threaded opening 217 can be a void 221 designed to accommodate stabilizers on the threaded rod, if used. While the threaded openings 217 can provide an adequate amount of leverage to locate the device 230, the addition of stabilizers on an installation instrument that contact the device 230 in the voids 221 can increase the ability of a surgeon to rotate the device during insertion. The rigid section 216 can be connected to an endplate 211 & 212 and/or to the body 213.

In some embodiments, the upper and lower endplates 211 & 212 are comprised of a lattice with a volumetric density between and including 60% and 100%. Embodiments of the device include examples where the endplates 211 & 212 are comprised of a lattice with a volumetric density between and including 80% and 100%, 70% and 90%, 60% and 64% and less than 60%. In some embodiments, the body 213 is comprised of a lattice with a volumetric density between and including 5% to 50%. Embodiments of the device include examples where the body 213 is comprised of a lattice with a volumetric density between and including 5% to 10%, 10% to 18%, 18% to 25%, 25% to 35% and 35% to 50%. In some examples, the lattice is comprised of a metallic scaffold. In others, the lattice is comprised of a scaffold comprised of titanium or an alloy thereof.

In some embodiments, the upper and lower endplates 211 & 112 are comprised of a lattice with an elastic modulus between and including 300 MPa to 130 GPa. Embodiments of the device include examples where the upper and lower endplates are comprised of a lattice with an elastic modulus between and including 300 MPa to 5 GPa, 1 GPa to 5 GPa, 5 GPa to 10 GPa, 10 GPa to 15 GPa., 15 GPa to 21 GPa and 21 GPa to 130 GPa. In some embodiments, the body 213 is comprised of a lattice with an elastic modulus between and including 10 MPa to 12 GPa. Embodiments of the device include examples where the body 113 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa and 8 GPa to 12 GPa. In another example, the body 213 is comprised of a lattice with an elastic modulus that is substantially similar to the bulk elastic modulus of the adjacent bone. In some examples, the lattice is comprised of a metallic scaffold. In others, the lattice is comprised of a scaffold comprised of titanium or an alloy thereof.

In FIGS. 24 to 30 is a second PLIF/TLIF implant 310 with an independent endplate structure. The second PLIF/TLIF implant 310 can be inserted between the endplates of two adjacent vertebrae, providing mechanical spacing between the endplates of the adjacent vertebrae and mechanical stability to promote bone growth, allowing the vertebrae to fuse together over time. The second PLIF/TLIF implant 310 can be comprised substantially of three components—an upper endplate 311, a lower endplate 312 and a body 313. The upper and lower endplates 311 & 312 can be comprised of a biocompatible material with a higher elastic modulus in the superior to inferior direction than the body 313. The body 313 can be comprised of a biocompatible material with a lower elastic modulus in the superior to inferior direction than the upper and lower endplates 311 & 312.

Figure 26:
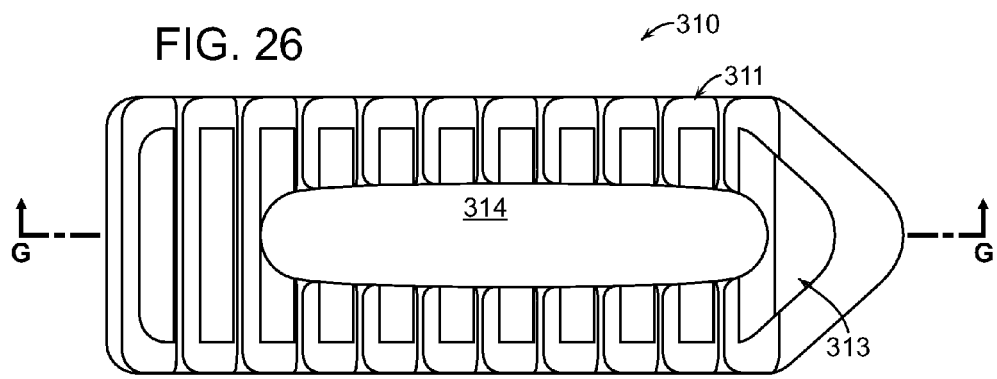
FIG. 26 is a top view of the second PLIF/TLIF implant showing a possible configuration of an endplate top surface and the location of a later presented section view.
Figure 27:
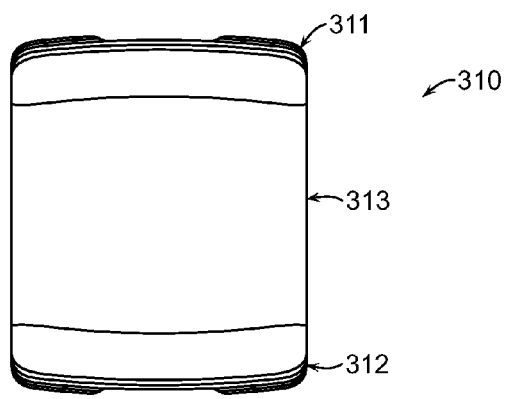
FIG. 27 is a rear view of the second PLIF/TLIF implant configured without a rear tool engagement area.
Figure 28:
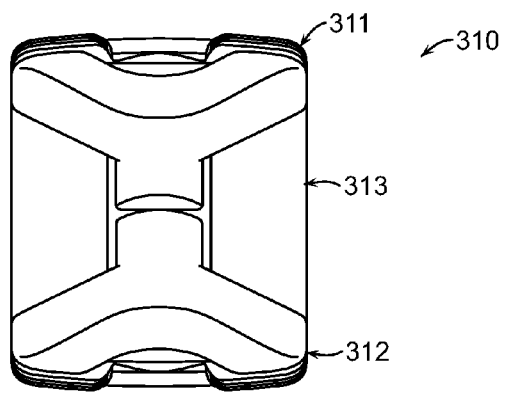
FIG. 28 is a front view of the second PLIF/TLIF implant showing the position of the endplates relative to one another.
Figure 29:
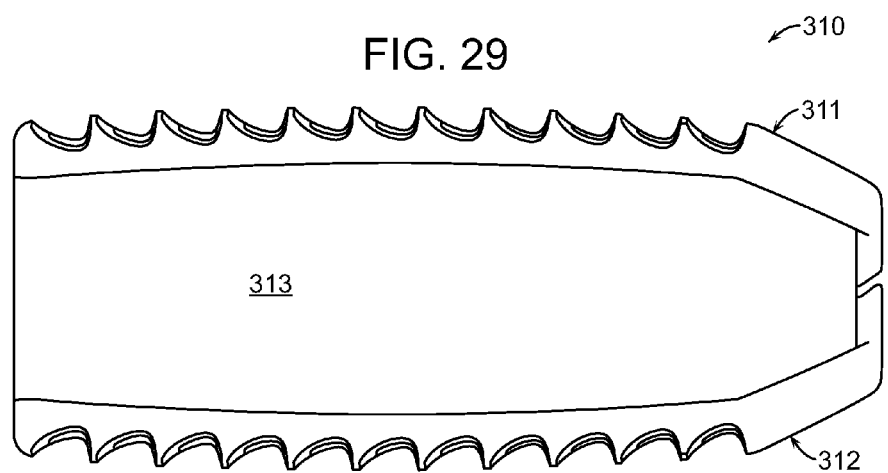
FIG. 29 is a side view of the second PLIF/TLIF implant also showing the position of the endplates relative to one another.
Figure 30:
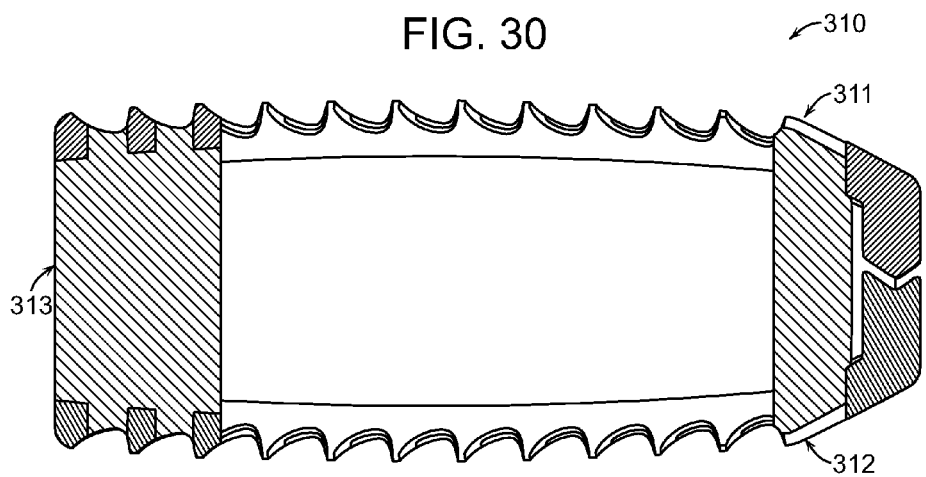
FIG. 30 is a side sectioned view of the second PLIF/TLIF, sectioned through line GG in FIG. 26.

In FIG. 24 is an isometric view of the second PLIF/TLIF implant 310, showing the independent configuration of the endplates 311 & 312 relative to the body 313. In FIG. 25 is an exploded isometric view of the second PLIF/TLIF implant 310, showing the endplates 311 & 312 separated from the body 313 and showing the lack of a direct and rigid connection between the endplates 311 & 312 in this embodiment. There may be direct connections between the endplates 311 & 312 to adjust the construct properties as long as the endplates 311 & 312 are capable of movement independent of one another. In FIG. 26 is a top view of the second PLIF/TLIF implant 310 showing an exemplary endplate configuration and identifying line and GG. In FIG. 27 is a rear view of the second PLIF/TLIF implant 310 detailing an example without an optional rear tool engagement area. In FIG. 28 is a front view of the second PLIF/TLIF implant 310 showing the position of the endplates relative to one another. In FIG. 29 is a side view of the second PLIF/TLIF implant 310, also showing the position of the endplates relative to one another. In FIG. 30 is a side sectioned view of the second PLIF/TLIF implant 310, sectioned through line GG in FIG. 26, showing that the endplates 311 & 312 do not directly contact one another throughout the device in this example.

The upper endplate 311 and lower endplate 312 are independent to one another with respect to their ability to move independently of one another. In some embodiments, the upper endplate 311 and lower endplate 312 are on opposite sides of the body 313 so that the endplates 311 & 312 can move independently of one another and where the amount of independent movement can be determined largely by the stiffness of the body 313. While a body is disclosed as a structure that can provide independence between endplates, other structures noted previously may provide a similar independence.

The body 313 preferably provides mechanical spacing between the adjacent vertebrae and provides adequate rigidity between the vertebrae to allow for bone ingrowth. The use of a body 313 with a lower elastic modulus than the endplates 311 & 312 can allow the new bone growth to be stressed while ingrowth occurs, resulting in a stronger fused bone. The relatively higher modulus of elasticity of the endplates 311 & 312 distributes the load across the surface of the body 313 and reduces the occurrence of the vertebral endplates from indenting the upper or lower surface of the body 313. In some examples, the endplates 311 & 312 use optional raised ridges or teeth 320 to mechanically anchor the endplates 311 & 312 to the endplates of the adjacent vertebrae. The ridges 320 can extend from the endplates 311 & 312 to the surface of the body 313 that extends to the superior and inferior surface of the device. In addition to distributing the load across the body 313 and anchoring the interbody fusion device 330 relative to the adjacent vertebrae, the endplates 311 & 312 can allow for bone attachment or ingrowth, providing stability between the interbody fusion device and the endplates of the adjacent vertebrae.

The interbody fusion device 310 also provides optional lumen 314 as a vertical bone fusion windows for radiolucency or bone fusion. The fusion window can be used by clinicians to insert one or more compounds that promote bone growth or to assess fusion through the lumen 314 during the healing process. Some compounds that would be appropriate for use in the fusion or viewing windows 314 are autograft, allograft synthetic graft, or a combination.

In some embodiments, the upper and lower endplates 311 & 312 are comprised of a lattice with a volumetric density between and including 60% and 100%. Embodiments of the device include examples where the endplates 311 & 312 are comprised of a lattice with a volumetric density between and including 80% and 100%, 70% and 90%, 60% and 64% and less than 60%. In some embodiments, the body 313 is comprised of a lattice with a volumetric density between and including 5% to 50%. Embodiments of the device include examples where the body 313 is comprised of a lattice with a volumetric density between and including 5% to 10%, 10% to 18%, 18% to 25%, 25% to 35% and 35% to 50%. In some examples, the lattice is comprised of a metallic scaffold. In others, the lattice is comprised of a scaffold comprised of titanium or an alloy thereof.

In some embodiments, the upper and lower endplates 311 & 312 are comprised of a lattice with an elastic modulus between and including 300 MPa to 130 GPa. Embodiments of the device include examples where the upper and lower endplates are comprised of a lattice with an elastic modulus between and including 300 MPa to 5 GPa, 1 GPa to 5 GPa, 5 GPa to 10 GPa, 10 GPa to 15 GPa., 15 GPa to 21 GPa and 21 GPa to 130 GPa. In some embodiments, the body 313 is comprised of a lattice with an elastic modulus between and including 10 MPa to 12 GPa. Embodiments of the device include examples where the body 313 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa and 8 GPa to 12 GPa. In another example, the body 313 is comprised of a lattice with an elastic modulus that is substantially similar to the bulk elastic modulus of the adjacent bone. In some examples, the lattice is comprised of a metallic scaffold. In others, the lattice is comprised of a scaffold comprised of titanium or an alloy thereof.

In FIGS. 31 to 37 is a third PLIF/TLIF implant 410 with an independent endplate structure. The third PLIF/TLIF implant 410 can be inserted between the endplates of two adjacent vertebrae, providing mechanical spacing between the endplates of the adjacent vertebrae and mechanical stability to promote bone growth, allowing the vertebrae to fuse together over time. The third PLIF/TLIF implant 410 can be comprised substantially of three components—an upper endplate 411, a lower endplate 412 and a body 413. The upper and lower endplates 411 & 412 can be comprised of a biocompatible material with a higher elastic modulus in the superior to inferior direction than the body 413. The body 413 can be comprised of a biocompatible material with a lower elastic modulus in the superior to inferior direction than the upper and lower endplates 411 & 412.

Figure 33:
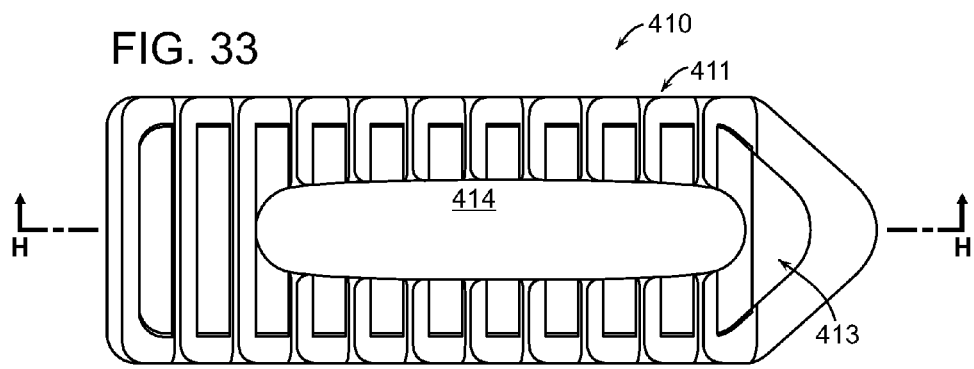
FIG. 33 is a top view of the third PLIF/TLIF implant showing a possible configuration of an endplate top surface and the location of a later presented section view.
Figure 34:
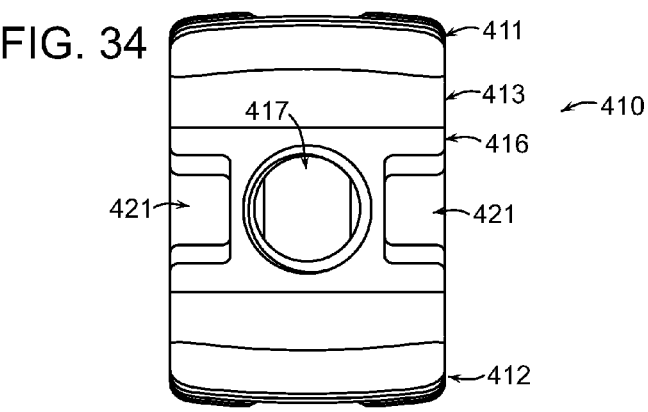
FIG. 34 is a rear view of the third PLIF/TLIF implant with an optional rear tool engagement area.
Figure 35:
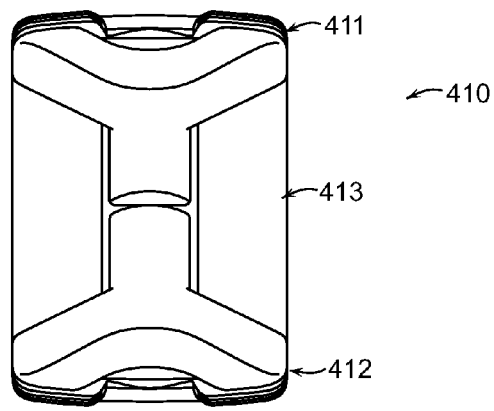
FIG. 35 is a front view of the third PLIF/TLIF implant showing the position of the endplates relative to one another.
Figure 36:
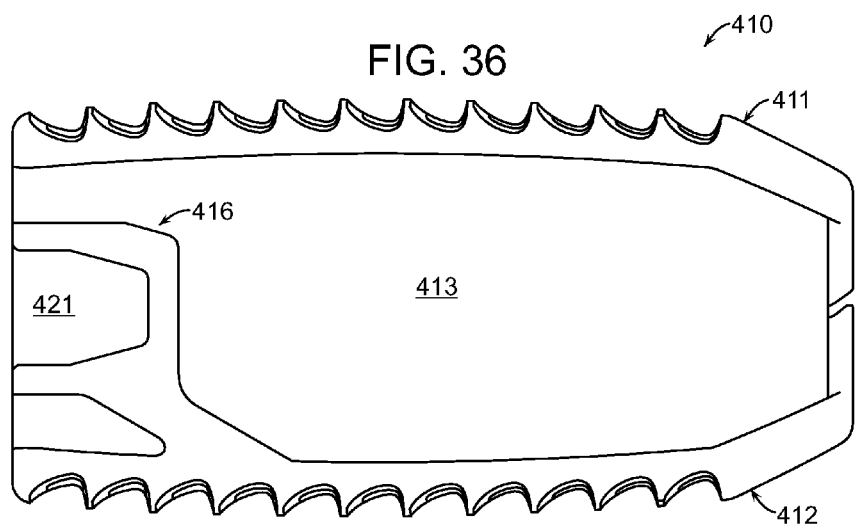
FIG. 36 is a side view of the third PLIF/TLIF implant also showing the position of the endplates relative to one another.
Figure 37:
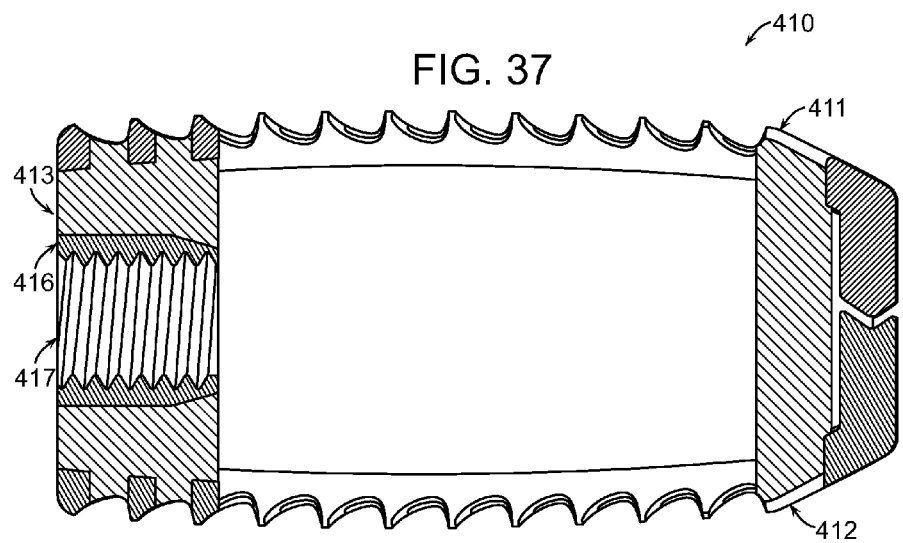
FIG. 37 is a side sectioned view of the third PLIF/TLIF, sectioned through line HH in FIG. 33.

In FIG. 31 is an isometric view of the third PLIF/TLIF implant 410, showing the independent configuration of the endplates 411 & 412 relative to the body 313. In FIG. 32 is an exploded isometric view of the third PLIF/TLIF implant 410, showing the endplates 411 & 412 separated from the body 413 and showing the lack of a direct and rigid connection between the endplates 411 & 412 in this embodiment. There may be direct connections between the endplates 411 & 412 to adjust the construct properties as long as the endplates 411 & 412 are capable of movement independent of one another. In FIG. 33 is a top view of the third PLIF/TLIF implant 410 showing an exemplary endplate configuration and identifying line and HH. In FIG. 34 is a rear view of the third PLIF/TLIF implant 410 showing the optional rear tool engagement area. In FIG. 35 is a front view of the third PLIF/TLIF implant 410 showing the position of the endplates relative to one another. In FIG. 36 is a side view of the third PLIF/TLIF implant 410, also showing the position of the endplates relative to one another. In FIG. 37 is a side sectioned view of the third PLIF/TLIF implant 410, sectioned through line HH in FIG. 33, showing that the endplates 411 & 412 do not directly contact one another throughout the device in this example.

The upper endplate 411 and lower endplate 412 are independent to one another with respect to their ability to move independently of one another. In some embodiments, the upper endplate 411 and lower endplate 412 are on opposite sides of the body 413 so that the endplates 411 & 412 can move independently of one another and where the amount of independent movement can be determined largely by the stiffness of the body 413. While a body is disclosed as a structure that can provide independence between endplates, other structures noted previously may provide a similar independence.

The body 413 preferably provides mechanical spacing between the adjacent vertebrae and provides adequate rigidity between the vertebrae to allow for bone ingrowth. The use of a body 113 with a lower elastic modulus than the endplates 411 & 412 can allow the new bone growth to be stressed while ingrowth occurs, resulting in a stronger fused bone. The relatively higher modulus of elasticity of the endplates 411 & 412 distributes the load across the surface of the body 413 and reduces the occurrence of the vertebral endplates from indenting the upper or lower surface of the body 413. In some examples, the endplates 411 & 412 use optional raised ridges or teeth 420 to mechanically anchor the endplates 411 & 412 to the endplates of the adjacent vertebrae. The ridges 420 can extend from the endplates 411 & 412 to the surface of the body 413 that extends to the superior and inferior surface of the device. In addition to distributing the load across the body 413 and anchoring the interbody fusion device 130 relative to the adjacent vertebrae, the endplates 411 & 412 can allow for bone attachment or ingrowth, providing stability between the interbody fusion device and the endplates of the adjacent vertebrae.

The third PLIF/TLIF implant 410 also provides optional lumen 414 as a vertical bone fusion windows for radiolucency or bone fusion. The fusion windows can be used by clinicians to insert one or more compounds that promote bone growth or to assess fusion through the lumen 414 during the healing process. Some compounds that would be appropriate for use in the fusion or viewing windows 414 and 415 are autograft, allograft synthetic graft, or a combination.

The lower endplate 412 of the third PLIF/TLIF implant 410 can include a substantially rigid section 416 to allow surgical tools to be fastened to the device 430 during a surgical procedure. In some examples, the rigid section 416 contains one or more threaded openings 417 that are configured to accept a threaded rod to facilitate placement of the device 410. On either side of each threaded opening 417 can be a void 421 designed to accommodate stabilizers on the threaded rod, if used. While the threaded openings 417 can provide an adequate amount of leverage to locate the device 410, the addition of stabilizers on an installation instrument that contact the device 410 in the voids 421 can increase the ability of a surgeon to rotate the device during insertion. The rigid section 416 can be connected to an endplate 411 & 412 and/or to the body 413.

In some embodiments, the upper and lower endplates 411 & 412 are comprised of a lattice with a volumetric density between and including 60% and 100%. Embodiments of the device include examples where the endplates 411 & 412 are comprised of a lattice with a volumetric density between and including 80% and 100%, 70% and 90%, 60% and 64% and less than 60%. In some embodiments, the body 413 is comprised of a lattice with a volumetric density between and including 5% to 50%. Embodiments of the device include examples where the body 413 is comprised of a lattice with a volumetric density between and including 5% to 10%, 10% to 18%, 18% to 25%, 25% to 35% and 35% to 50%. In some examples, the lattice is comprised of a metallic scaffold. In others, the lattice is comprised of a scaffold comprised of titanium or an alloy thereof.

In some embodiments, the upper and lower endplates 411 & 412 are comprised of a lattice with an elastic modulus between and including 300 MPa to 130 GPa. Embodiments of the device include examples where the upper and lower endplates are comprised of a lattice with an elastic modulus between and including 300 MPa to 5 GPa, 1 GPa to 5 GPa, 5 GPa to 10 GPa, 10 GPa to 15 GPa., 15 GPa to 21 GPa and 21 GPa to 130 GPa. In some embodiments, the body 413 is comprised of a lattice with an elastic modulus between and including 10 MPa to 12 GPa. Embodiments of the device include examples where the body 413 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa and 8 GPa to 12 GPa. In another example, the body 413 is comprised of a lattice with an elastic modulus that is substantially similar to the bulk elastic modulus of the adjacent bone. In some examples, the lattice is comprised of a metallic scaffold. In others, the lattice is comprised of a scaffold comprised of titanium or an alloy thereof.

In FIGS. 38 to 42 is a vertebral body replacement or corpectomy (hereinafter "VBR") implant 540 with an independent endplate structure. The VBR implant 540 can be inserted between the endplates of two vertebrae, providing mechanical spacing between the endplates of the vertebrae and mechanical stability to promote bone growth, allowing the vertebrae to fuse together over time. The VBR implant 540 can be comprised substantially of three components—an upper endplate 511, a lower endplate 512 and a body 513. The upper and lower endplates 511 & 512 can be comprised of a biocompatible material with a higher elastic modulus than the body 513. The body 513 can be comprised of a biocompatible material with a lower elastic modulus than the upper and lower endplates 511 & 512.

Figure 38:
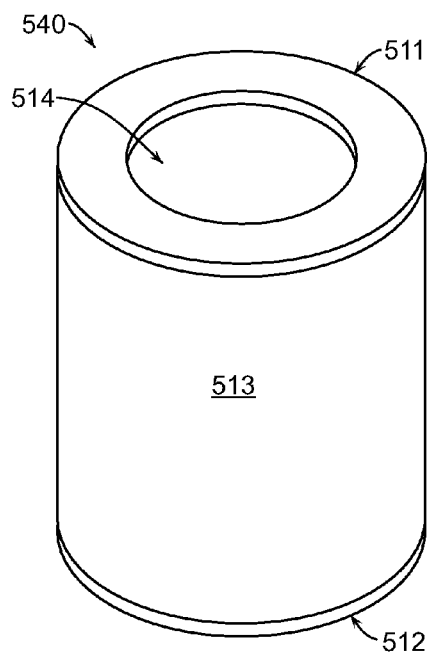
FIG. 38 is an isometric view of a vertebral body replacement (hereinafter "VBR") implant showing the inventive configuration of the endplates relative to the body on the exterior of the device.
Figure 39:
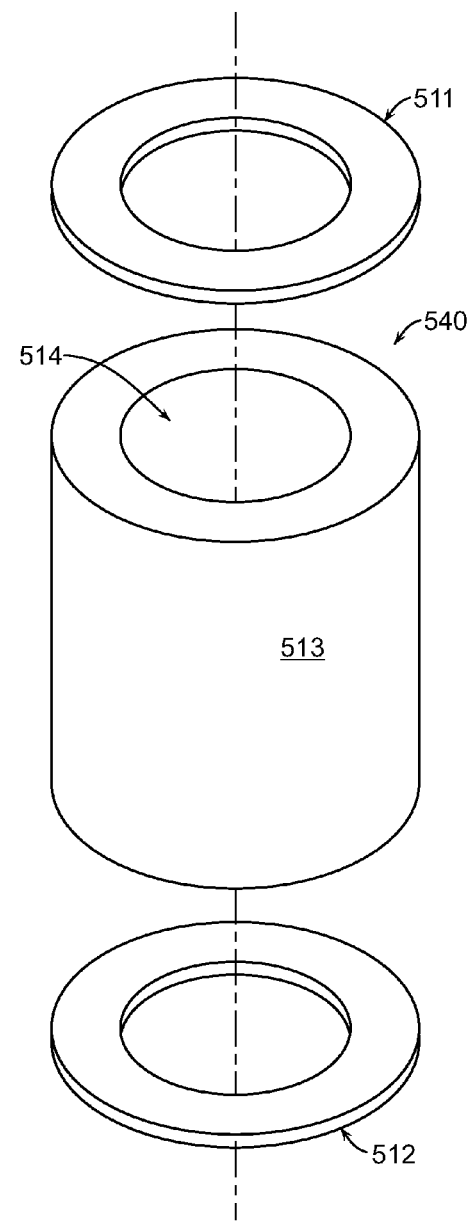
FIG. 39 is an exploded isometric view of the VBR implant showing the endplates separated from the body.
Figure 42:
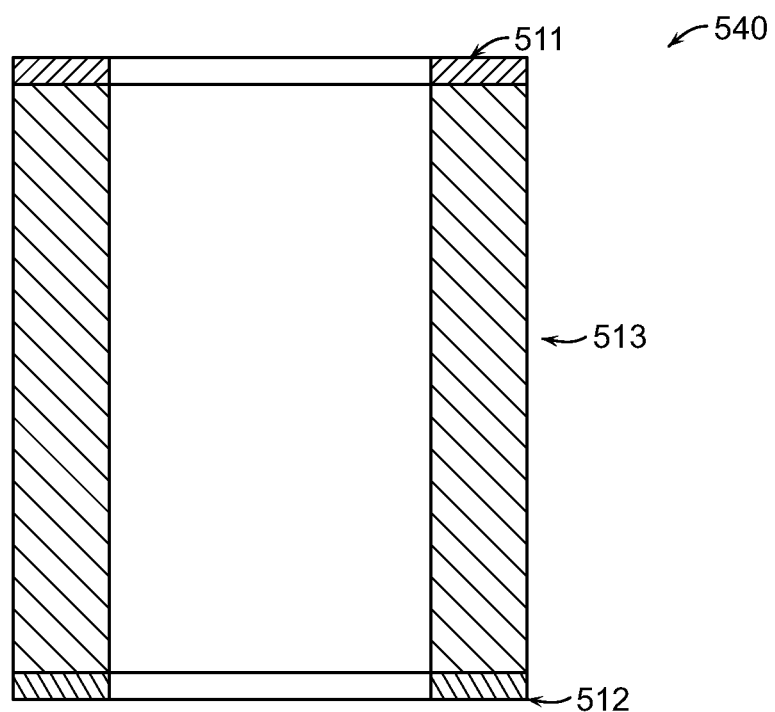
FIG. 42 is a side sectioned view of the VBR implant, sectioned through line HH in FIG. 40.

In FIG. 38 is an isometric view of the VBR implant 540, showing the independent configuration of the endplates 511 & 512 relative to the body 513. In FIG. 39 is an exploded isometric view of the VBR implant 540, showing the endplates 511 & 512 separated from the body 513 and showing the lack of a direct and rigid connection between the endplates 511 & 512 in this embodiment. There may be direct connections between the endplates 511 & 512 to adjust the construct properties as long as the endplates 511 & 512 are capable of movement independent of one another. In FIG. 40 is a top view of the VBR implant 540 showing an exemplary endplate configuration and identifying line II. In FIG. 41 is a rear view of the VBR implant 540 showing the position of the endplates relative to one another. In FIG. 42 is a side sectioned view of the VBR implant 540, sectioned through line II in FIG. 40 showing that the endplates 511 & 512 do not directly contact one another throughout the device in this example.

The upper endplate 511 and lower endplate 512 are independent to one another with respect to their ability to move independently of one another. In some embodiments, the upper endplate 511 and lower endplate 512 are on opposite sides of the body 513 so that the endplates 511 & 512 can move independently of one another and where the amount of independent movement can be determined largely by the stiffness of the body 513. While a body is disclosed as a structure that can provide independence between endplates, other structures noted previously may provide a similar independence.

The body 513 preferably provides mechanical spacing of the implant site and provides adequate rigidity to allow for bone ingrowth. The use of a body 513 with a lower elastic modulus than the endplates 511 & 512 can allow the new bone growth to be stressed while ingrowth occurs, resulting in a stronger fused bone. The relatively higher modulus of elasticity of the endplates 511 & 512 distributes the load across the surface of the body 513 and prevents the indentation of the upper or lower surface of the body 513. In some examples, the endplates 511 & 512 use optional raised ridges or teeth to mechanically anchor the endplates 511 & 512 and prevent expulsion. The endplates 511 & 512 can allow for bone attachment or ingrowth, providing stability between the implant and the patient's bone.

The VBR implant 540 also provides optional lumen 514 as a vertical bone fusion window for radiolucency or bone fusion. The fusion window can be used by clinicians to insert one or more compounds that promote bone growth or to assess fusion through the lumen 514 during the healing process. Some compounds that would be appropriate for use in the fusion or viewing windows 514 and 515 are autograft, allograft, synthetic graft, or a combination.

In some embodiments, the upper and lower endplates 511 & 512 are comprised of a lattice with a volumetric density between and including 60% and 100%. Embodiments of the device include examples where the endplates 511 & 512 are comprised of a lattice with a volumetric density between and including 80% and 100%, 70% and 90%, 60% and 64% and less than 60%. In some embodiments, the body 513 is comprised of a lattice with a volumetric density between and including 5% to 50%. Embodiments of the device include examples where the body 513 is comprised of a lattice with a volumetric density between and including 5% to 10%, 10% to 18%, 18% to 25%, 25% to 35% and 35% to 50%. In some examples, the lattice is comprised of a metallic scaffold. In others, the lattice is comprised of a scaffold comprised of titanium or an alloy thereof.

In some embodiments, the upper and lower endplates 511 & 512 are comprised of a lattice with an elastic modulus between and including 300 MPa to 130 GPa. Embodiments of the device include examples where the upper and lower endplates are comprised of a lattice with an elastic modulus between and including 300 MPa to 5 GPa, 1 GPa to 5 GPa, 5 GPa to 10 GPa, 10 GPa to 15 GPa., 15 GPa to 21 GPa and 21 GPa to 130 GPa. In some embodiments, the body 513 is comprised of a lattice with an elastic modulus between and including 10 MPa to 12 GPa. Embodiments of the device include examples where the body 513 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa and 8 GPa to 12 GPa. In another example, the body 513 is comprised of a lattice with an elastic modulus that is substantially similar to the elastic modulus of the adjacent bone. In some examples, the lattice is comprised of a metallic scaffold. In others, the lattice is comprised of a scaffold comprised of titanium or an alloy thereof.

In FIGS. 43 to 49 is an osteotomy wedge 650 with an independent endplate structure. The osteotomy wedge 650 can be inserted in or between bones to provide mechanical spacing and mechanical stability to promote bone growth. The osteotomy wedge 650 can be comprised substantially of three components—an upper endplate 611, a lower endplate 612 and a body 613. The upper and lower endplates 611 & 612 can be comprised of a biocompatible material with a higher elastic modulus than the body 613. The body 613 can be comprised of a biocompatible material with a lower elastic modulus than the upper and lower endplates 611 & 612.

Figure 45:
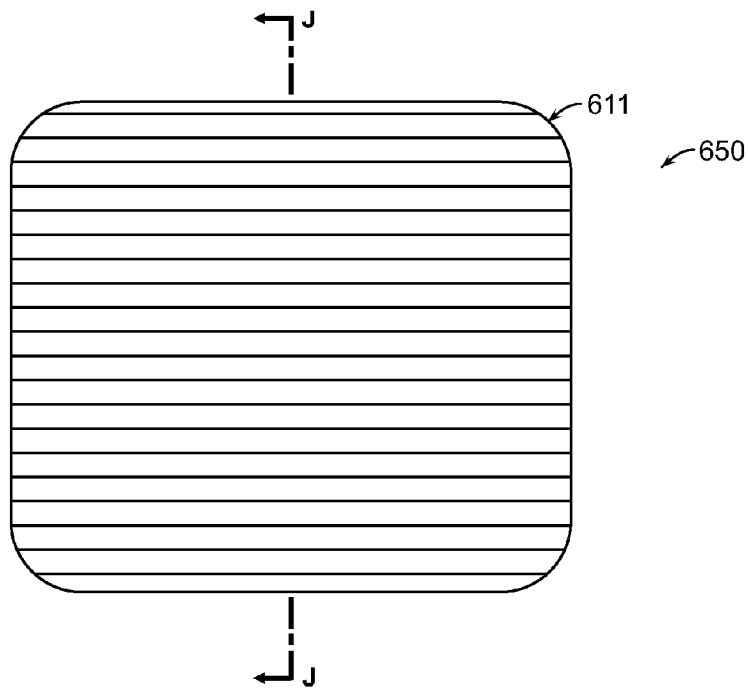
FIG. 45 is a top view of the osteotomy wedge showing a possible configuration of an endplate top surface and the location of a later presented section view.
Figure 46:
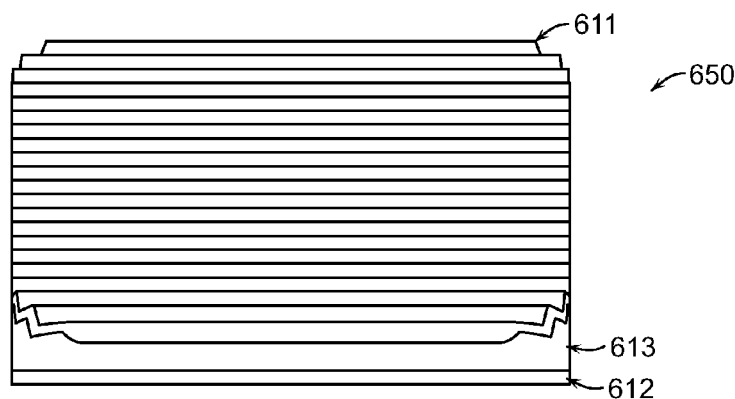
FIG. 46 is a rear view of the osteotomy wedge configured without a tool engagement area.
Figure 47:
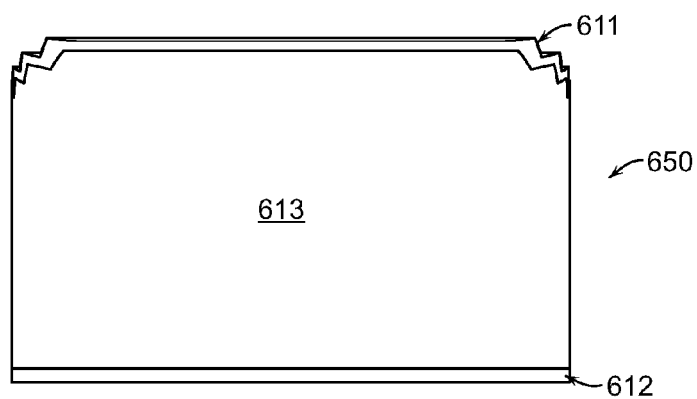
FIG. 47 is a front view of the osteotomy wedge showing the position of the endplates relative to one another.
Figure 48:
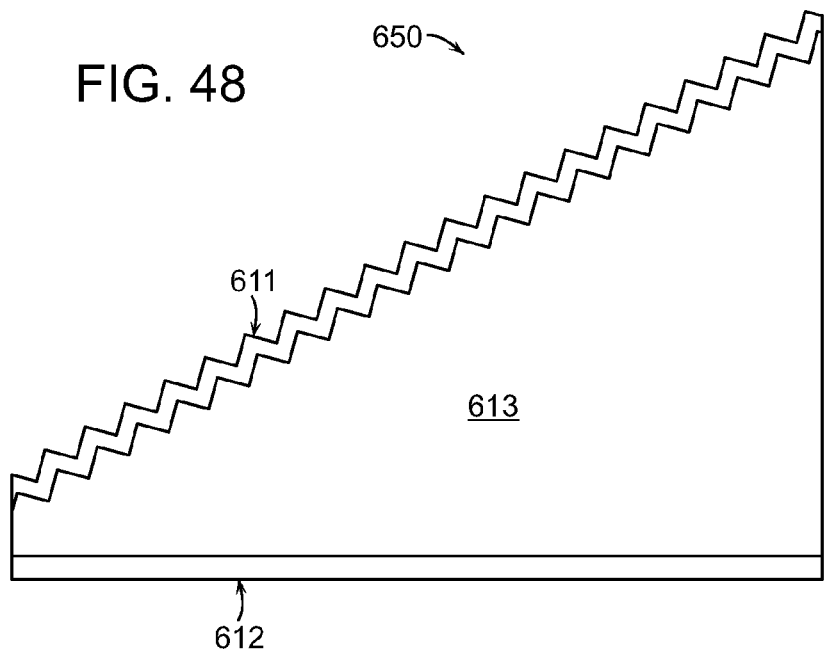
FIG. 48 is a side view of the osteotomy wedge also showing the position of the endplates relative to one another.
Figure 49:
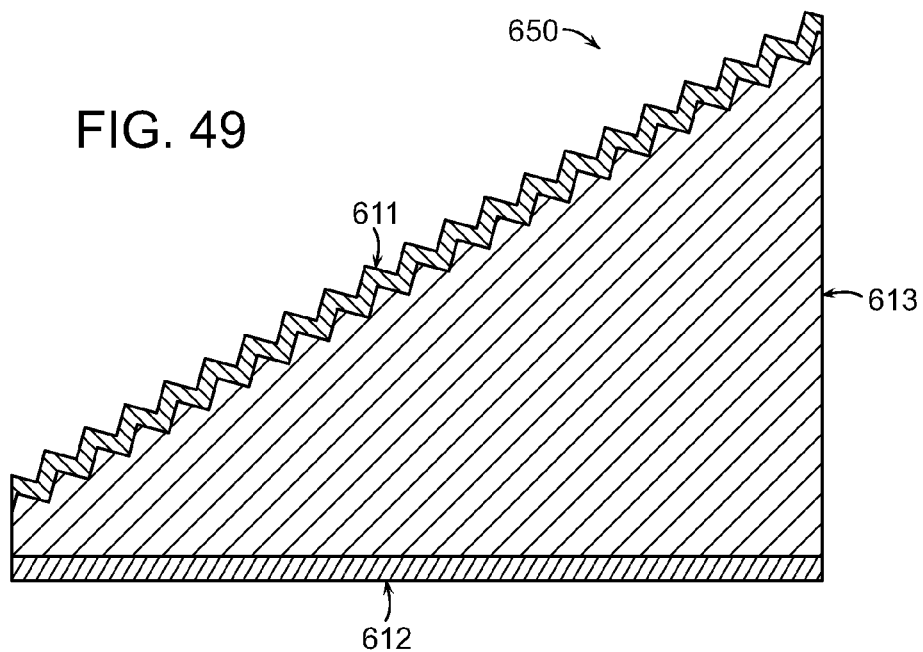
FIG. 49 is a side sectioned view of the osteotomy wedge, sectioned through line II in FIG. 45.

In FIG. 43 is an isometric view of the osteotomy wedge 650, showing the independent configuration of the endplates 611 & 612 relative to the body 613. In FIG. 44 is an exploded isometric view of the osteotomy wedge 650, showing the endplates 611 & 612 separated from the body 613 and showing the lack of a direct and rigid connection between the endplates 611 & 612 in this embodiment. There may be direct connections between the endplates 611 & 612 to adjust the construct properties as long as the endplates 611 & 612 are capable of movement independent of one another. In FIG. 45 is a top view of the osteotomy wedge 650 showing an exemplary endplate configuration and identifying line JJ. In FIG. 46 is a rear view of the osteotomy wedge 650. In FIG. 47 is a front view of the osteotomy wedge 650 showing the position of the endplates relative to one another. In FIG. 48 is a side view of the osteotomy wedge 650, also showing the position of the endplates relative to one another. In FIG. 49 is a side sectioned view of the osteotomy wedge 650, sectioned through line JJ in FIG. 45 and showing that the endplates 611 & 612 do not directly contact one another throughout the device in this example.

The upper endplate 611 and lower endplate 612 are independent to one another with respect to their ability to move independently of one another. In some embodiments, the upper endplate 611 and lower endplate 612 are on opposite sides of the body 613 so that the endplates 611 & 612 can move independently of one another and where the amount of independent movement can be determined largely by the stiffness of the body 613. While a body is disclosed as a structure that can provide independence between endplates, other structures noted previously may provide a similar independence.

The body 613 preferably provides mechanical spacing of the implant site and provides adequate rigidity to allow for bone ingrowth. The use of a body 613 with a lower elastic modulus than the endplates 611 & 612 can allow the new bone growth to be stressed while ingrowth occurs, resulting in a stronger fused bone. The relatively higher modulus of elasticity of the endplates 611 & 612 distributes the load across the surface of the body 613 and prevents the indentation of the upper or lower surface of the body 613. In some examples, the endplates 611 & 612 use optional raised ridges or teeth to mechanically anchor the endplates 611 & 612 and prevent expulsion. The endplates 611 & 612 can allow for bone attachment or ingrowth, providing stability between the implant and the patient's bone.

In some embodiments, the upper and lower endplates 611 & 612 are comprised of a lattice with a volumetric density between and including 60% and 100%. Embodiments of the device include examples where the endplates 611 & 612 are comprised of a lattice with a volumetric density between and including 80% and 100%, 70% and 90%, 60% and 64% and less than 60%. In some embodiments, the body 613 is comprised of a lattice with a volumetric density between and including 5% to 50%. Embodiments of the device include examples where the body 613 is comprised of a lattice with a volumetric density between and including 5% to 10%, 10% to 18%, 18% to 25%, 25% to 35% and 35% to 50%. In some examples, the lattice is comprised of a metallic scaffold. In others, the lattice is comprised of a scaffold comprised of titanium or an alloy thereof.

In some embodiments, the upper and lower endplates 611 & 612 are comprised of a lattice with an elastic modulus between and including 300 MPa to 130 GPa. Embodiments of the device include examples where the upper and lower endplates are comprised of a lattice with an elastic modulus between and including 300 MPa to 5 GPa, 1 GPa to 5 GPa, 5 GPa to 10 GPa, 10 GPa to 15 GPa., 15 GPa to 21 GPa and 21 GPa to 130 GPa. In some embodiments, the body 613 is comprised of a lattice with an elastic modulus between and including 10 MPa to 12 GPa. Embodiments of the device include examples where the body 613 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa and 8 GPa to 12 GPa. In another example, the body 613 is comprised of a lattice with an elastic modulus that is substantially similar to the bulk elastic modulus of the adjacent bone. The body 613 may also have an elastic modulus gradient matching the slope to maintain constant stiffness across the length. In some examples, the lattice is comprised of a metallic scaffold. In others, the lattice is comprised of a scaffold comprised of titanium or an alloy thereof.

For the exemplary embodiments disclosed above and for other implants, certain ranges of elastic moduli for the body and endplates appear to optimize bone growth in implants of a given construct elastic modulus range and comprised of a lattice structure.

Table 1 represents the ideal ranges of elastic moduli for the body and endplates in implants of a given construct elastic modulus range. Table 1 is calculated for a first endplate height of 2.5 mm, a body height of 2.0 mm and a second endplate height of 2.5 mm. Table 2 represents the preferential ranges of elastic moduli for the body and endplates in implants with a first endplate height of 1.5 mm, a body height of 4.0 mm, a second endplate height of 1.5 mm and within a given construct elastic modulus range. Table 3 represents the preferential ranges of elastic moduli for the body and endplates in implants with a first endplate height of 2.5 mm, a body height of 2.0 mm, a second endplate height of 2.5 mm and within a given construct elastic modulus range. Table 4 represents the most preferential ranges of elastic moduli for the body and endplates in PLIF/TLIF implants with a first endplate height of 2.5 mm, a body height of 2.0 mm, a second endplate height of 2.5 mm and within a given construct elastic modulus range. Table 5 represents the most preferential ranges of elastic moduli for the body and endplates in ALIF implants with a first endplate height of 2.5 mm, a body height of 6.0 mm, a second endplate height of 2.5 mm and within a given construct elastic modulus range.

The values given for the body and endplate elastic moduli for a given range of construct elastic moduli provide the ideal relationship between the stiffness of the endplates to the body to optimize bone growth. It is theorized that the increased loading of new bone growth stimulates bone growth and results in stronger bone growth. The use of the inventive implant structure and values allow for the use of a lower elastic modulus body protected by higher elastic modulus endplates to allow for a large volume of bone loading. The relationships given in Tables 1 to 5 can be applied to multiple types of implants of various footprint areas and heights. The tables and equations disclosed herein are intended to provide heights and elastic moduli for an implant at an actual stiffness. Since the tables and equations are based on an actual or as-tested stiffness value, they may be adjusted to include an adjustment factor for a method of manufacture. For instance, if a specific additive process is known to produce an implant with an actual stiffness that is 90% of the calculated value, the tables and equations can include an adjustment to compensate for this difference.

The method disclosed herein uses elastic modulus to approximate the bending stiffness of the endplates, however, their bending stiffness may be changed using equivalent methods. For examples, instead of reducing the volumetric density of an endplate, cutouts can be provided to reduce the integrity of the endplate. The use of partial cutouts on the outer surface of an endplate can serve to reduce its bending stiffness and provide anti-expulsion properties for the implant. The area of the endplates can also be reduced to reduce their bending stiffness. Where the footprint area of an implant is the area of the implant when viewed from above, less the area of any lumen, the endplate area can be between and including 10% to 100% of the footprint area. In general, the use of an endplate with an area less than the footprint would require the elastic modulus of the endplate to be increased.

The construct elastic modulus of an implant is related to the stiffness of an implant in the following equation:

$$K_{UBL} = A * E_{UBL}/L_{UBL}$$

Where:

$K_{UBL}$=Construct stiffness in the vertical direction (N/m), where the vertical direction is the direction from one endplate to another endplate A=Average footprint area of the construct less the area of the lumen, if any (m$^2$)

$E_{UBL}$=Modulus of elasticity of construct (GPa)

$L_{UBL}$=Height of the construct (m)

Because the stiffness of an implant is dependent on the average construct footprint area, construct elastic modulus and the construct height, any one of these may be adjusted to change the stiffness. The method disclosed herein optimizes the composition of the construct elastic modulus between that of the endplates and body, but because of the relationship between the stiffness and average construct footprint, the optimal ranges may be adjusted by changing the average construct footprint.

The modulus of elasticity of an implant is dependent on the height of the implant, the height and modulus of elasticity of the body, and the height and modulus of elasticity of the endplates. In an implant with one body and two endplates, the construct modulus of elasticity is generally represented by the following equation:

$$E_{UBL} = L_{UBL}/(L_U/E_U + L_L/E_L + L_B/E_B)$$

Where:

$E_{UBL}$=Modulus of elasticity of construct (GPa)
$L_{UBL}$=Height of the construct (m)
$L_U$=Height of a first endplate (m)
$E_U$=Modulus of elasticity of a first endplate (GPa)
$L_L$=Height of a second endplate (m)
$E_L$=Modulus of elasticity of a second endplate (GPa)
$L_B$=Height of the body (m)
$E_B$=Modulus of elasticity of the body (GPa)

The stiffness, footprint area and height of a construct may be predetermined values, potentially related to patient anatomy or standard sizes, so that the height of each endplate, modulus of elasticity of the endplates, the height of the body, and the modulus of elasticity of the body must be calculated. Since the body is generally much taller than the height of the endplates, the body's elastic modulus is the main driver in determining the construct's elastic modulus. With the body's elastic modulus as the main driver in construct elastic modulus, the body's elastic modulus is often near that of the construct. It has been found that varying the endplate elastic moduli relative to that of the body, within certain ranges, optimizes the stiffness of the endplates relative to that of the body within a range of given construct values.

As apparent in the equations provided above, the stiffness of a material is a function of its elastic modulus, height and area. The height and area of an implant are generally given, in that they are specified based on a patient's need (i.e. size of implant location). In some cases, the construct elastic modulus or stiffness can be specified as well, resulting in a need to determine an appropriate elastic modulus and height for the body and endplates. In some cases, if the endplates and/or the body do not have the same footprint area as the construct, the area of each may also need to the be selected.

For each range of construct elastic moduli, a range of elastic moduli are given for the body and endplates because a range of values can be appropriate by changing the elastic modulus of each layer. For instance, if the elastic modulus of the body is reduced with all other variables remaining the same, the elastic modulus of the endplates would need to be increased to retain the same construct elastic modulus. Increasing the height of a layer with a homogenous elastic modulus generally increases that layer's impact on construct modulus. Therefore, it is possible to reduce the thickness of the endplate, while increasing its elastic modulus to maintain a level construct modulus. The opposite is also possible so that the height of the body may be increased and its elastic modulus reduced to maintain a level construct modulus.

TABLE 1

Body and Endplate Elastic Moduli Ranges
for Certain Construct Elastic Modulus Ranges
Where:
$L_B$ = 2.0 mm
$L_U$ = 2.5 mm
$L_L$ = 2.5 mm

| Minimum construct elastic modulus (GPa) | Maximum construct elastic modulus (GPa) | Minimum body elastic modulus (GPa) | Maximum body elastic modulus (GPa) | Minimum endplate elastic modulus (GPa) | Maximum endplate elastic modulus (GPa) |
|---|---|---|---|---|---|
| 0.01 | 2.5 | 0.0029 | 2.5 | 0.01 | 22 |
| 2.5 | 6 | 0.71 | 6 | 2.5 | 130 |
| 6 | 15 | 1.71 | 15 | 6 | 130 |
| 15 | 22 | 4.3 | 22 | 15 | 130 |
| 22 | 130 | 6.3 | 130 | 22 | 130 |

The preferential values given in Tables 2 & 3 apply a preferential range to the body elastic modulus for a given construct elastic modulus range. It has been theorized that the optimal body elastic modulus falls between and including 60% to 80% of the construct's elastic modulus. For example, a construct with an elastic modulus of 10 GPa would optimally have a body elastic modulus of 6 GPa to 8 GPa. In some examples, the optimal body elastic modulus falls between and including 60% to 100% of the construct's elastic modulus. In some examples, it may be beneficial to select a body elastic modulus between and including 50% to 100% the construct elastic modulus. It would be possible to achieve a body elastic modulus with the same elastic modulus as the construct in a given direction (such as the axial direction of the spine) if the endplates have preferential stiffness.

TABLE 2

Preferential Body and Endplate Elastic
Moduli Ranges for Certain Construct Elastic
Modulus Ranges
Where:
$L_B$ = 4.0 mm
$L_U$ = 1.5 mm
$L_L$ = 1.5 mm

| Minimum construct elastic modulus (GPa) | Maximum construct elastic modulus (GPa) | Minimum body elastic modulus (GPa) | Maximum body elastic modulus (GPa) | Minimum endplate elastic modulus (GPa) | Maximum endplate elastic modulus (GPa) |
|---|---|---|---|---|---|
| 0.01 | 2.5 | 0.006 | 2 | 0.01 | 13 |
| 2.5 | 6 | 1.5 | 4.8 | 2.5 | 108 |
| 6 | 15 | 3.6 | 12 | 6 | 130 |
| 15 | 22 | 9 | 17.6 | 15 | 130 |
| 22 | 130 | 13.2 | 88 | 22 | 130 |

TABLE 3

Preferential Body and Endplate Elastic
Moduli Ranges for Certain Construct Elastic
Modulus Ranges
Where:
$L_B$ = 2.0 mm
$L_U$ = 2.5 mm
$L_L$ = 2.5 mm

| Minimum construct elastic modulus (GPa) | Maximum construct elastic modulus (GPa) | Minimum body elastic modulus (GPa) | Maximum body elastic modulus (GPa) | Minimum endplate elastic modulus (GPa) | Maximum endplate elastic modulus (GPa) |
|---|---|---|---|---|---|
| 0.01 | 2.5 | 0.006 | 2 | 0.01 | 22 |
| 2.5 | 6 | 1.5 | 4.8 | 2.5 | 130 |
| 6 | 15 | 3.6 | 12 | 6 | 130 |
| 15 | 22 | 9 | 17.6 | 15 | 130 |
| 22 | 130 | 13.2 | 88 | 22 | 130 |

TABLE 4

Most Preferential Body and Endplate
Elastic Moduli Ranges for Certain PLIF/TLIF
Construct Elastic Modulus Ranges
Where:
$L_B$ = 2.0 mm
$L_U$ = 2.5 mm
$L_L$ = 2.5 mm

| Minimum construct elastic modulus (GPa) | Maximum construct elastic modulus (GPa) | Minimum body elastic modulus (GPa) | Maximum body elastic modulus (GPa) | Minimum endplate elastic modulus (GPa) | Maximum endplate elastic modulus (GPa) |
|---|---|---|---|---|---|
| 0.3 | 2.2 | 0.2 | 2.2 | 0.3 | 3.0 |
| 2.2 | 3.5 | 1.3 | 3.5 | 2.2 | 4.7 |
| 3.5 | 4.0 | 2.1 | 4.0 | 3.5 | 5.4 |

TABLE 5

Most Preferential Body and Endplate
Elastic Moduli Ranges for Certain ALIF Construct
Elastic Modulus Ranges
Where:
$L_B$ = 6.0 mm
$L_U$ = 2.5 mm
$L_L$ = 2.5 mm

| Minimum construct elastic modulus (GPa) | Maximum construct elastic modulus (GPa) | Minimum body elastic modulus (GPa) | Maximum body elastic modulus (GPa) | Minimum endplate elastic modulus (GPa) | Maximum endplate elastic modulus (GPa) |
|---|---|---|---|---|---|
| 0.1 | 0.9 | 0.08 | 0.9 | 0.1 | 8.9 |
| 0.3 | 2.2 | 0.2 | 2.2 | 0.3 | 3.0 |
| 2.2 | 3.5 | 1.3 | 3.5 | 2.2 | 4.7 |
| 3.5 | 4.0 | 2.1 | 4.0 | 3.5 | 5.4 |

Using Tables 1 to 5 and the equations disclosed above, an optimized body and endplate elastic modulus can be calculated. For instance, for an implant with a construct elastic modulus of 10 MPa, an endplate thickness of 1.5 mm, a body height of 7 mm and a body elastic modulus of 6 MPa, the endplates optimally have an elastic modulus of 90 MPa. Additional examples of endplate elastic modulus calculations are included below in Table 6 where the construct elastic modulus, endplate thickness, body height and body elastic modulus are preselected. While the examples given solve for the endplate modulus of elasticity, it is known within the art that the endplate modulus of elasticity could be a preselected value and the inventive process could be used to determine a different variable. The examples in Table 6 use a body elastic modulus value that is 70% that of the construct elastic modulus.

TABLE 6

Examples of Endplate Elastic Modulus Calculations

| Construct Elastic Modulus (GPa) | 0.01 | 0.165 | 0.3 | 1.2 | 2.5 | 4 |
|---|---|---|---|---|---|---|
| Endplate thickness (mm) | 1.5 | 1.5 | 1.5 | 1.5 | 1.5 | 1.5 |
| Body Height (mm) | 4 | 4 | 4 | 4 | 4 | 4 |
| Body Elastic Modulus (GPa) | 0.007 | 0.12 | 0.21 | 0.84 | 1.8 | 2.8 |
| Endplate Elastic Modulus (GPa) | 0.022 | 0.37 | 0.67 | 2.7 | 5.6 | 8.9 |
| Construct Elastic Modulus (GPa) | 6 | 12 | 15 | 18 | 22 | |
| Endplate thickness (mm) | 1.5 | 1.5 | 1.5 | 1.5 | 1.5 | |
| Body Height (mm) | 7 | 7 | 7 | 7 | 7 | |
| Body Elastic Modulus (GPa) | 4.2 | 0.84 | 10.5 | 12.6 | 15.4 | |
| Endplate Elastic Modulus (GPa) | 13.4 | 36 | 33.5 | 40.2 | 49.2 | |

In some embodiments, the elastic modulus of the endplate is a known or fixed value. For instance, for an implant with a construct elastic modulus of 18 GPa, an endplate thickness of 1.5 mm, a body height of 4.0 mm and an endplate elastic modulus of 40.2 GPa, the body optimally has an elastic modulus of approximately 12.6 GPa. The examples and tables disclosed herein can be used to generate a complete implant or just a portion of an implant. If used to generate a portion of an implant, additional layers may be added to endplates to provide additional integration surfaces or anti-expulsion devices.

In some embodiments, the elastic modulus of the body is merely less than the elastic modulus of one endplate. The endplates are preferably less vulnerable to indentation than the body. While vulnerability to indentation is generally related to elastic modulus, in some examples, the endplates can have a lower elastic modulus than the body, but maintain a higher resistance to indentation than the body through the use of an alternate material, structure or other variable. In other embodiments, the endplates are connected to one another with a link or connection with a lower elastic modulus than that of the endplates. A lower elastic modulus link could be accomplished through the use of a body, a spring or other material capable of elastic deformation under load disposed between the endplates.

In some embodiments, it can be beneficial to provide a modulus of elasticity gradient between the endplates and body so that the modulus of elasticity changes over a particular distance. The use of a modulus of elasticity gradient in an implant can increase the shear strength of the implant along the plane separating the endplate from the body. The use of a modulus of elasticity gradient can occur over a distance of multiple unit cells or within a single unit cell.

In some embodiments, a structure other than the body provides mechanical separation between the endplates. In such embodiments, the body can be a nonstructural lattice or scaffold and the mechanical separation may be provided by a spring or other structure capable of elastic deformation between the endplates.

In some embodiments, the body is comprised of closed cell lattice structure or impermeable structure to prevent the ingrowth of bone or tissue. In implants that are intended to be temporary, it can be beneficial to prevent bone or tissue ingrowth to ease later removal. In examples that are designed for ease of removal, the body may also be comprised of a material with an appropriate elastic modulus when its volumetric density approaches 100%. An outer impermeable layer may also be provided on the surface of an open cell structure to prevent ingrowth or attachment. It is also possible to use a coating to prevent bone growth or attachment to an implant.

Some embodiments are comprised, in whole or in part, of a randomly generated lattice structure. Lattice structures may be comprised of struts and openings that are randomly generated within certain parameters rather than by repeating a unit cell. Some examples include a body comprised of a randomly generated lattice structure with internal openings ranging between and including 100 to 700 μm in size. Other examples can include a body comprised of a randomly generated lattice structure with internal openings averaging between and including 420 to 450 μm in size. Other examples can include a body comprised of a randomly generated lattice structure with a volumetric density between and including 38 to 62%. Some examples can include a body comprised of a randomly generated lattice structure with a volumetric density between and including 38 to 42%. Some examples can include a body comprised of a randomly generated lattice structure with a volumetric density between and including 58 to 62%.

What has been described is an independent endplate structure that can provide various benefits when used in an implant. In this disclosure, there is shown and described only the preferred embodiment of the invention, but, as aforementioned, it is to be understood that the invention is capable of use in various other combinations and environments and is capable of changes or modifications within the scope of the inventive concept as expressed herein.

What is claimed is:

1. A bone fusion implant comprising:
a body comprising a metallic lattice structure; and
a first endplate spaced apart from a second endplate, the first end plate being mechanically connected to the second endplate only via the body;
wherein:
said first endplate comprises an upper surface for contacting a first segment of bone and a lower surface fixed to said body;
said second endplate comprises a lower surface for contacting a second segment of bone and an upper surface fixed to said body;
wherein an elastic modulus of each of the first endplate and second endplate is higher than an elastic modulus of the body; and
wherein the body is disposed at least partially between the first and second endplates; and
each of said first and second endplates comprises a metal.

2. The device of claim 1 wherein at least one of said endplates comprises one or more interconnected openings having a volumetric density between and including 60 percent to 90 percent.

3. The device of claim 1, wherein said body has a volumetric density between and including 5 percent to 50 percent.

4. The device of claim 3, wherein said body has a volumetric density between and including 5 percent to 18 percent.

5. The device of claim 3, wherein said body has a volumetric density between and including 25 percent to 35 percent.

6. The device of claim 1, wherein said first endplate, said second endplate and said body comprise titanium or an alloy thereof.

7. The device of claim 1, wherein both of said first endplate and said second endplate have one or more interconnected openings.

8. The device of claim 1, wherein said body has an elastic modulus between and including 300 MPa to 12 GPa.

9. The device of claim 1, wherein said first endplate and said second endplate have an elastic modulus between and including 300 MPa to 130 GPa.

10. The device of claim 1, wherein said body has an elastic modulus between and including 50 percent to 100 percent of a construct elastic modulus of said implant.

11. The device of claim 10, wherein said body has an elastic modulus between and including 300 MPa to 2 GPa.

12. The device of claim 10, wherein said body has an elastic modulus between and including 1 GPa to 5 GPa.

13. The device of claim 1, wherein said bone fusion implant has a construct elastic modulus between and including 0.3 GPa to 4 GPa, said body has an elastic modulus between and including 0.375 GPa to 4 GPa and said first endplate and said second endplate have an elastic modulus between and including 0.3 GPa to 5.4 GPa.

14. The bone fusion implant of claim 1, wherein said first and second endplates comprise different metals.

15. The bone fusion implant of claim 1, wherein said metal of any of said body and said endplates is selected from the group consisting of zirconium, stainless steel, tantalum, nitinol, cobalt, chromium alloys, titanium and tungsten, and alloys thereof.

16. The bone fusion implant of claim 1, wherein each of said first and second endplate comprises an annular ring having a width and a length substantially equal to a width and a length of implant's footprint.

17. The bone fusion implant of claim 16, wherein said first endplate has an area, when viewed from above, that is 10 percent to 100 percent the implant footprint area.

18. The bone fusion implant of claim 1, wherein at least one of said endplates comprises a plurality of ridges for mechanically anchoring said at least one endplate to an adjacent vertebrae.

19. The bone fusion implant of claim 1, further comprising one or more impact rails fixed to at least one of the endplates and extending rearward.

20. The bone fusion implant of claim 1, wherein said upper endplate has a continuous area, when viewed from above, that is 30 percent to 40 percent the implant footprint area.

* * * * *